United States Patent
Chen et al.

(10) Patent No.: US 10,806,431 B2
(45) Date of Patent: Oct. 20, 2020

(54) APPLICATION SPECIFIC INTEGRATED CIRCUIT WITH COLUMN-ROW-PARALLEL ARCHITECTURE FOR ULTRASONIC IMAGING

(71) Applicant: Massachusetts Institute of Technology, Cambridge, MA (US)

(72) Inventors: Kailiang Chen, Cambridge, MA (US); Charles G. Sodini, Belmont, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1435 days.

(21) Appl. No.: 14/497,150

(22) Filed: Sep. 25, 2014

(65) Prior Publication Data

US 2015/0087991 A1    Mar. 26, 2015

Related U.S. Application Data

(60) Provisional application No. 61/882,113, filed on Sep. 25, 2013, provisional application No. 61/928,456, filed on Jan. 17, 2014.

(51) Int. Cl.
*A61B 8/00* (2006.01)
*H03F 3/45* (2006.01)
(Continued)

(52) U.S. Cl.
CPC .......... *A61B 8/4488* (2013.01); *B06B 1/0207* (2013.01); *B06B 1/0215* (2013.01); *G01S 7/5202* (2013.01); *G01S 7/5208* (2013.01); *G01S 7/52025* (2013.01); *G01S 7/52033* (2013.01); *G01S 15/8925* (2013.01); *G01S 15/8993* (2013.01); *G01S 15/8995* (2013.01); *G10K 11/346* (2013.01); *H03F 3/45076* (2013.01); *A61B 8/13* (2013.01); *A61B 8/483* (2013.01); *A61B 8/54* (2013.01); *B06B 2201/20* (2013.01); *B06B 2201/51* (2013.01);
(Continued)

(58) Field of Classification Search
None
See application file for complete search history.

(56) References Cited

FOREIGN PATENT DOCUMENTS

| EP | 2533241 A2 | 12/2012 |
|---|---|---|
| WO | 03001571 A2 | 1/2003 |

OTHER PUBLICATIONS

Chen et al. "A column row parallel ASIC architecture for 3D wearable/portable medical ultrasonic imaging", IEEE, 2014.*
(Continued)

*Primary Examiner* — Carolyn A Pehlke
*Assistant Examiner* — Marjan Saboktakin
(74) *Attorney, Agent, or Firm* — Talem IP Law, LLP

(57) ABSTRACT

An ultrasonic imaging system is described in which a column-row-parallel architecture is provided at the circuit level of an ultrasonic transceiver. The ultrasonic imaging system can include a N×M array of transducer elements and a plurality of transceiver circuits where each transceiver circuit is connected to a corresponding one transducer element of the N×M array of transducer elements. A shared pulser gate driver and a shared VGA is provided for each row and column. Selection logic includes row select, column select, and per-element bit select. Through the column-row-parallel architecture, a variety of aperture configurations can be achieved.

17 Claims, 29 Drawing Sheets

(51) Int. Cl.
*G01S 7/52* (2006.01)
*G01S 15/89* (2006.01)
*G10K 11/34* (2006.01)
*B06B 1/02* (2006.01)
*A61B 8/13* (2006.01)
*A61B 8/08* (2006.01)

(52) U.S. Cl.
CPC ....... *B06B 2201/55* (2013.01); *B06B 2201/76* (2013.01); *H03F 2200/375* (2013.01); *H03F 2203/45224* (2013.01)

(56) References Cited

OTHER PUBLICATIONS

"Invitation to Pay Additional Fees and, Where Applicable, Protest Fee" issued in International Application No. PCT/US2014/057536, dated Jan. 5, 2015; 9 pages.

"Notification of Transmittal of the International Search Report and the Written Opinion of the International Searching Authority, or the Declaration" issued in International Application No. PCT/US2014/057536, dated Apr. 15, 2015; 20 pages.

"An Integrated Circuit with Transmit Beamforming and Parallel Receive Channels for Real-Time Three Dimensional Ultrasound Imaging" by Ira Wygant, et al.; 2006 IEEE Ultrasonics Symposium; 4 pages.

"Two Approaches to Electronically Scanned 3D Imaging Using cMUTs" by Chris Daft, et al.; 2006 IEEE Ultrasonics Symposium; 4 pages.

"A Column-Row-Parallel ASIC Architecture for 3D Wearable / Portable Medical Ultrasonic Imaging" by Kailiang Chen, et al.; 2014 Symposium on VLSI Circuits Digest of Technical Papers; 2 pages.

Bhuyan, et al., "3D volumetric ultrasound imaging with a 32×32 CMUT array integrated with front-end ICs using flip-chip bonding technology," ISSCC Dig. Tech. Papers, pp. 396-397, Feb. 2013.

Savord, et al., "Fully sampled matrix transducer for real time 3D ultrasonic imaging," IEEE Ultrasonics Symposium, pp. 945-953, Oct. 2003.

Wygant et al., "Integration of 2D CMUT Arrays with Front-End Electronics for Volumetric Ultrasound Imaging," IEEE UFFC, Feb. 2008.

Seo, et al., "A 256 × 256 2-D array transducer with row-column addressing for 3-D rectilinear imaging," IEEE UFFC, Apr. 2009.

Chen, et al., "Ultrasonic Imaging Transceiver Design for CMUT: A 3-Level 30Vpp Pulse-Shaping Pulser with Improved Efficiency and a Noise-Optimized Receiver," accepted, IEEE JSSC, Nov. 2013.

Montaldo, et al., "Coherent plane-wave compounding for very high frame rate ultrasonography and transient elastography," IEEE UFFC, Mar. 2009.

Bianchi, et al., "A 90Vpp 720MHz GBW linear power amplifier for ultrasound imaging transmitters in BCD6-SOI." ISSCC Dig. Tech. Papers, pp. 370-372, Feb. 2012.

Nikoozadeh, "Intracardiac ultrasound imaging using capacitive micromachined ultrasonic transducer (cmut) arrays," Ph.D. dissertation, Stanford University, 2010.

Gurun, et al., "Front-end receiver electronics for high-frequency monolithic cmut-on-cmos imaging arrays," IEEE UFFC, pp. 1658-1668, Aug. 2011.

Chen, et al., "Ultrasonic Imaging Front-End Design for CMUT: A 3-Level 30Vpp Pulse-Shaping Pulser with Improved Efficiency and a Noise-Optimized Receiver," IEEE ASSCC, 2012.

* cited by examiner

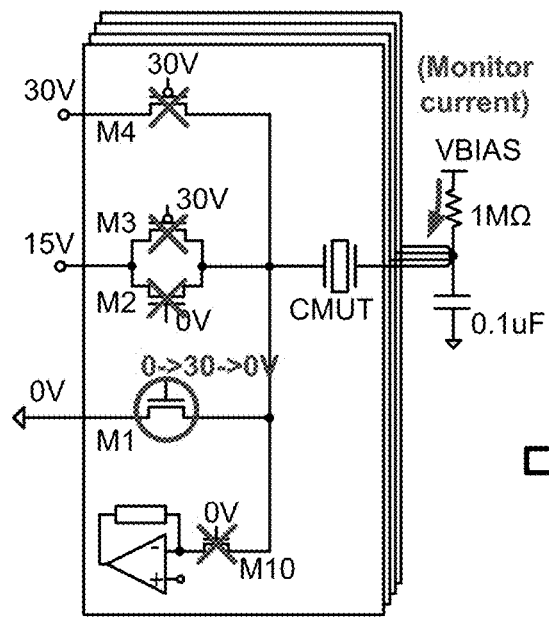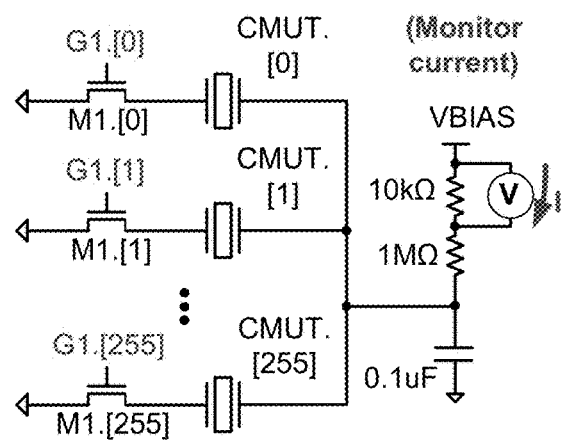
FIG. 9A   FIG. 9B
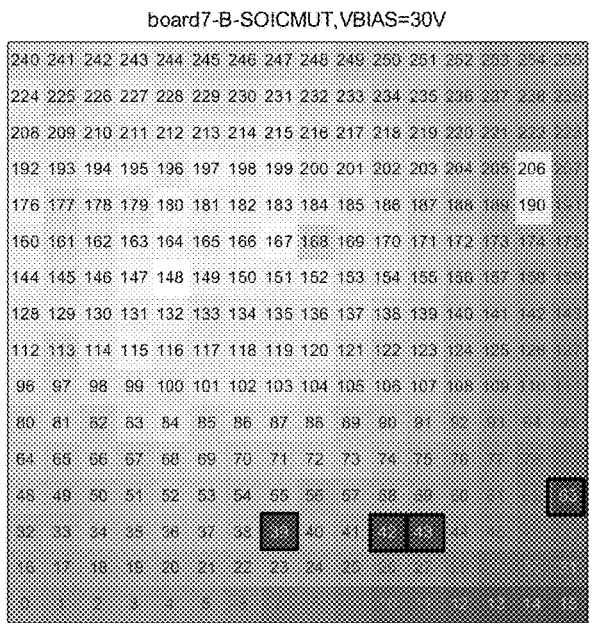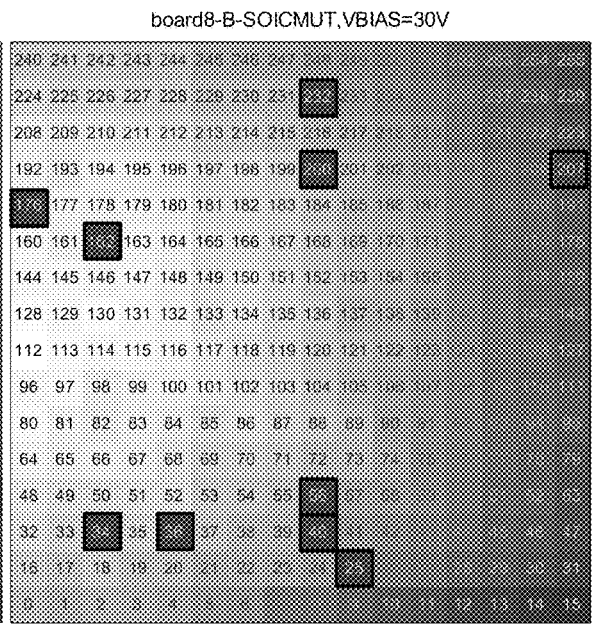
FIG. 9C   FIG. 9D

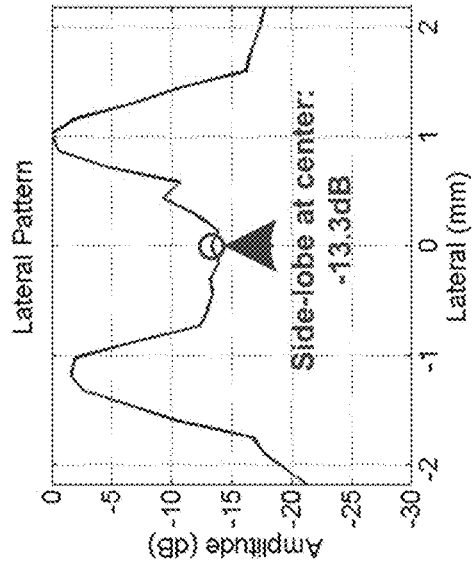
FIG. 14C
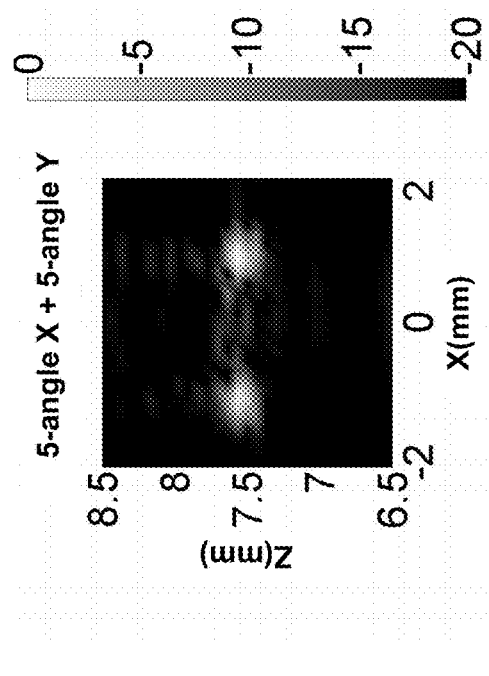
FIG. 14B
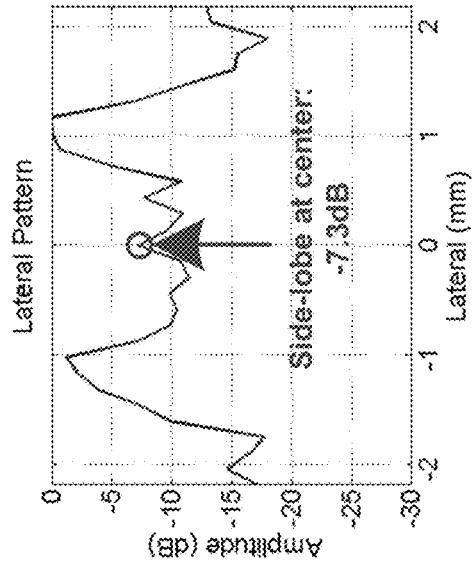
FIG. 14E
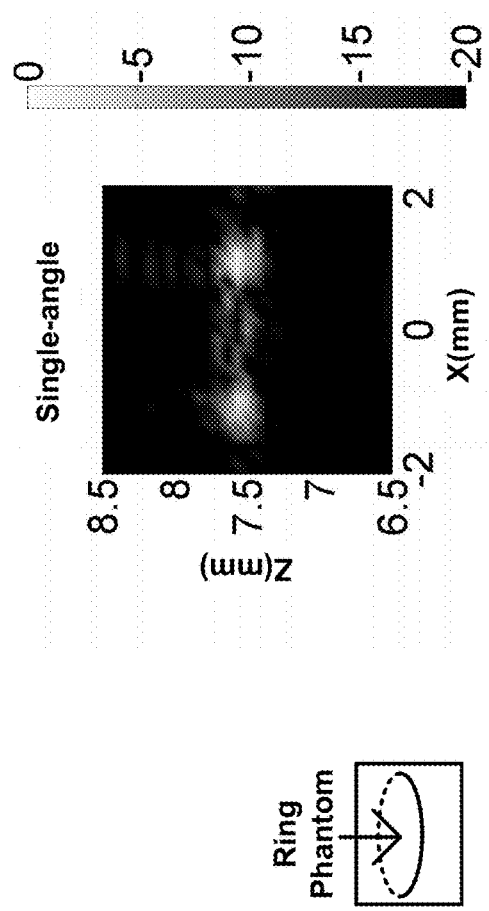
FIG. 14D
FIG. 14A

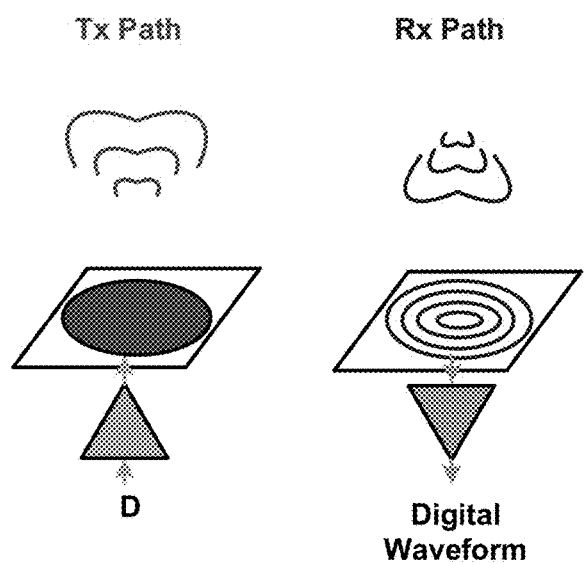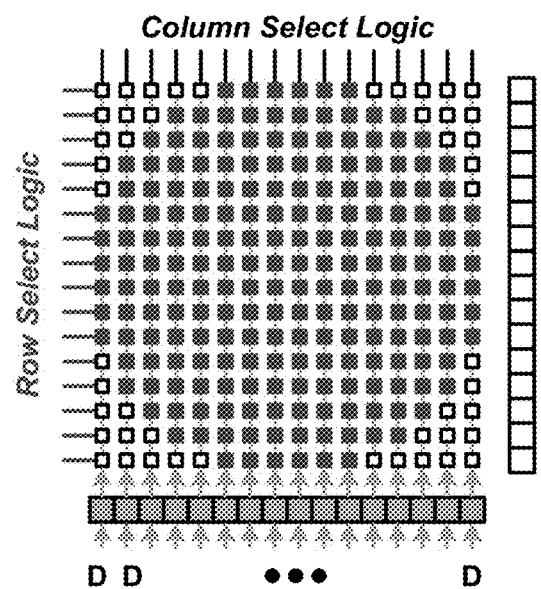
FIG. 18A
FIG. 18B
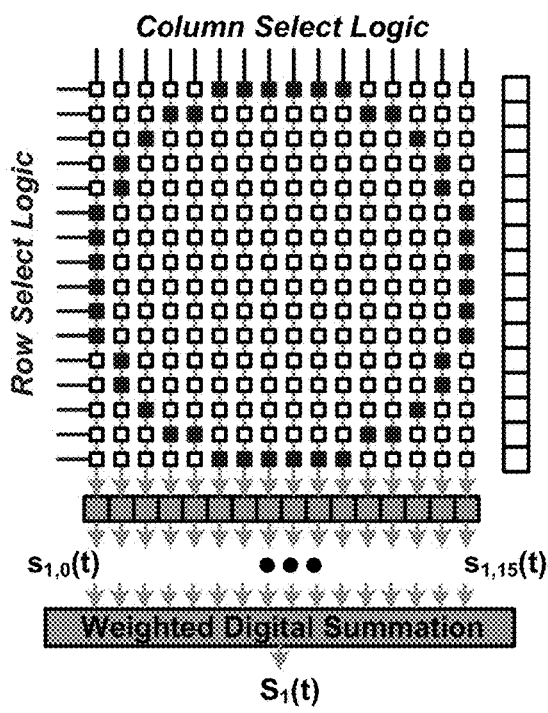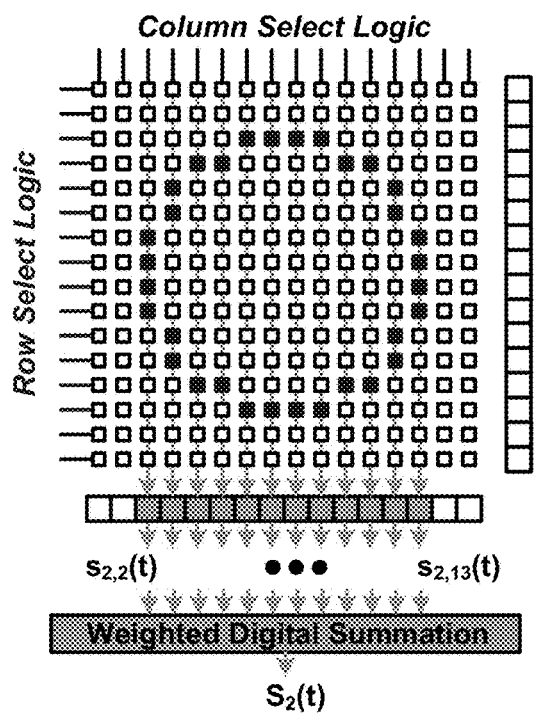
FIG. 18C
FIG. 18D

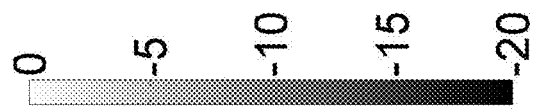
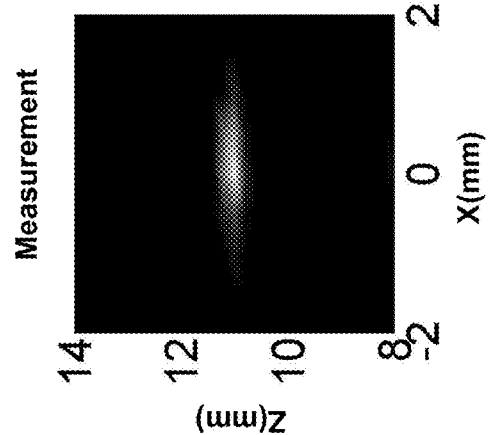
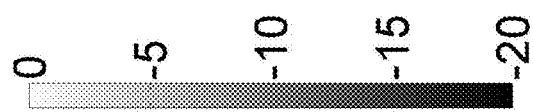
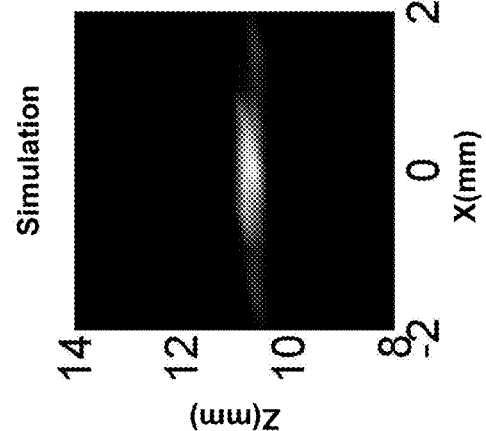
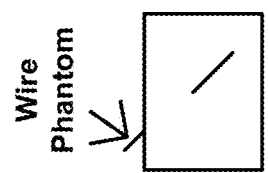
FIG. 21A  FIG. 21B  FIG. 21C
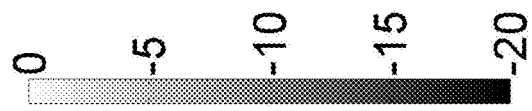
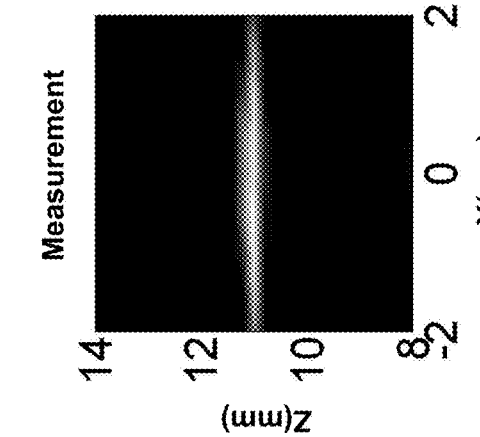
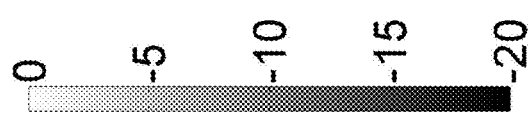
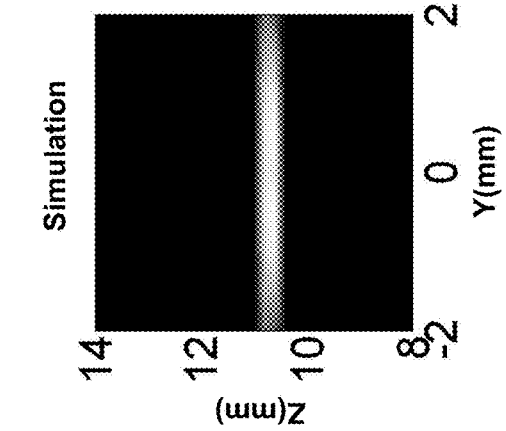
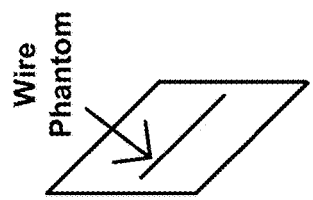
FIG. 22A  FIG. 22B  FIG. 22C

APPLICATION SPECIFIC INTEGRATED CIRCUIT WITH COLUMN-ROW-PARALLEL ARCHITECTURE FOR ULTRASONIC IMAGING

CROSS-REFERENCE TO RELATED APPLICATIONS

This application claims the benefit under 35 U.S.C. § 119 of Provisional Patent Application No. 61/882,113, filed Sep. 25, 2013, and Provisional Patent Application No. 61/928,456, filed Jan. 17, 2014, which are hereby incorporated by reference in their entirety.

BACKGROUND

Ultrasound imaging has numerous applications, particularly in the field of medicine. Ultrasound imaging, sometimes referred to as sonography, enables the visualization of soft tissues such as muscles and internal organs. Three-dimensional (3D) ultrasound imaging provides a volumetric view of the soft tissues, which can be sufficiently comprehensive to facilitate diagnosing and monitoring of the condition of tissues of interest. A 3D ultrasound imaging system may involve two-dimensional (2D) transducer arrays, mechanical localizers, or freehand scanning with automated localization. In such systems, volume information may be acquired directly or by assigning 3D spatial coordinates to a series of continuous or non-continuous 2D images. Continuous acquisition of 3D volume data, sometimes referred to as 4D ultrasound may also be desirable in certain applications.

Miniaturization of ultrasound imaging systems is possible through the use of micro-electro-mechanical systems (MEMS) technology. Capacitive micro-machined ultrasonic transducers (CMUTs) and piezoelectric micro-machined ultrasonic transducers (PMUTs) are two examples of silicon MEMS-based devices that may be incorporated in ultrasound imaging systems. Thus, whether a dynamic representation of a tissue volume over a specified time interval (4D ultrasound) or a volumetric view of the tissue captured at a particular time (3D ultrasound) is performed, it is possible to provide a full view of human tissue or organ in space using a portable—and even wearable—monitoring unit.

BRIEF SUMMARY

An ultrasonic imaging system is described in which a column-row-parallel architecture is provided at the circuit level of an ultrasonic transceiver. Through the column-row-parallel architecture, a variety of aperture configurations can be achieved including plane-wave coherent compounding, checkerboard patterns, and annular rings.

An ultrasonic imaging system with column-row-parallel architecture includes a N×M array of transducer elements; and a plurality of transceiver circuits. Each transceiver circuit is connected to a corresponding one transducer element of the N×M array of transducer elements. Each row and column of transceiver circuits share a common transmitter driver and a common variable gain amplifier (VGA) buffer, which can include an automatic offset cancelation feature.

A VGA buffer with automatic offset cancelation includes at least one differential amplifier; and a cancelation loop connected at an output of one of the at least one differential amplifier, or at the output of an analog-to-digital converter (ADC) with digitized signal, to an input of a second of the at least one differential amplifier.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 9A and 9B are schematics illustrating a process of detecting shorts in a CMUT array using the fault-tolerant feature enabled by the described architecture.

FIGS. 9C and 9D illustrate two example assemblies with the short elements marked with a box

FIG. 14A shows a representation indicating that the volumetric images of the metal ring phantom are shown as a cross-sectional image of a vertical slice.

FIG. 14B shows the vertical slice image from a single-angle Tx plane wave.

FIG. 14C shows the vertical slice from compounded plane-waves (compound of azimuth and elevation).

FIG. 14D shows a lateral resolution plot of the single-angle ring image.

FIG. 14E shows a lateral resolution plot from the compounded image showing suppressed side-lobes.

FIGS. 18A-18F illustrate an example annular ring configuration.

FIG. 21A shows a representation indicating that the volumetric images of the wire phantom are shown as a cross-sectional image of the wire (XZ plane).

FIG. 21B shows the cross-sectional slice image from a simulated XZ slice.

FIG. 21C shows the cross-sectional slice image from the measured XZ slice.

FIG. 22A shows a representation indicating that the volumetric images of the wire phantom are shown as a vertical cross-section of a longitudinal image of the wire (YZ plane).

FIG. 22B shows the cross-sectional slice image from a simulated YZ slice.

FIG. 22C shows the cross-sectional slice image from the measured YZ slice.

DETAILED DISCLOSURE

An ultrasonic imaging system is described in which a column-row-parallel architecture is provided at the circuit level of an ultrasonic transceiver. Through the column-row-parallel architecture, a variety of aperture configurations can be achieved.

Figure 1:
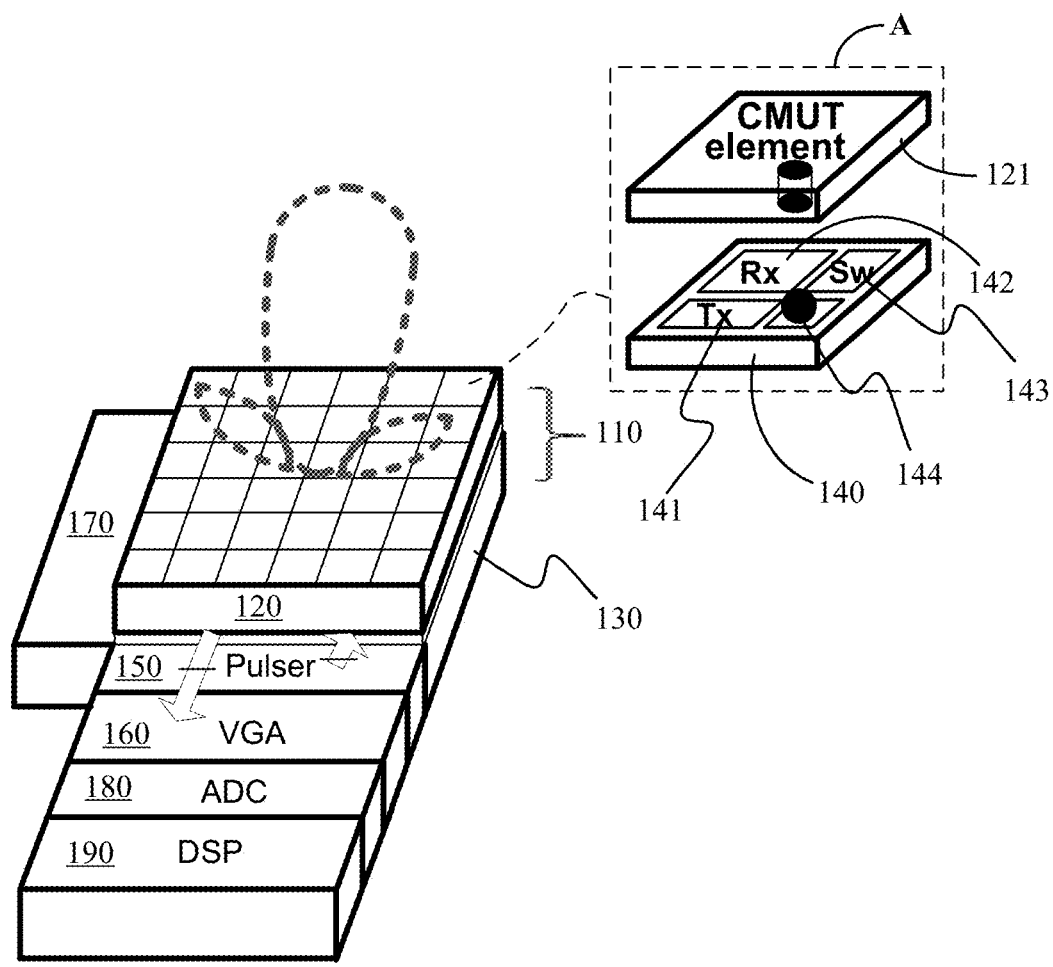
FIG. 1 illustrates an example of a compact ultrasound device with an ultrasonic transceiver having a circuit-level column-row-parallel architecture.

FIG. 1 illustrates an example of a compact ultrasound device with an ultrasonic transceiver having a circuit-level column-row-parallel architecture. Referring to FIG. 1, a compact ultrasound device 100 may include an ultrasonic transceiver 110 with an ultrasonic transducer array 120 on an application-specific integrated circuit (ASIC) 130. The ASIC 130 includes a transceiver element 140 corresponding to each transducer element 121 of the transducer array 120 (see inset image A). A fully column-row-parallel configuration for the transducers is possible through connecting a transceiver element 140 of the ASIC 130 to each of the transducer elements 121.

The transceiver element 140 includes a transmitter pulser circuit 141, a receiver low noise amplifier (LNA) 142, and selection logic 143. The output of the transmitter pulser circuit 141 is connected (via connection 144) to the transducer element 121 and receives a pulse signal through shared pulser gate drivers 150. The pulser gate drivers 150 include both drivers that are shared by a row of transceiver elements 140 and drivers that are shared by a column of transceiver elements 140. The receiver LNA 142 is selectively connected (via connection 144) to the transducer element 121 in order to output a received signal to a shared variable gain amplifier (VGA) buffer 160. Similar to the configuration for the pulser gate drivers 150, the VGAs 160 are connected to the rows and the columns of transceiver elements 140.

The selection logic 143 enables individual selection of a particular transceiver element 140 when column select logic and row select logic are driven by control logic 170. The selection logic 143 further controls connection of the transmitter pulser circuit 141 and receiver LNA 142 to each transceiver element 140 according to transmit/receive mode. The ASIC 130 can further include an analog-to-digital converter (ADC) 180 and a digital signal processor (DSP) 190.

The ultrasonic transducer array 120 can be a capacitive micro-machined ultrasonic transducer (CMUT), a piezo-electric micro-machined ultrasonic transducer (PMUT), or any other suitable 2D array of transducers for 3D imaging. A detailed explanation and specific implementations using a CMUT are provided herein; however, it should be understood that the described ASIC architecture and imaging techniques are applicable to any suitable ultrasonic transducer array 120.

A 2D CMUT includes a two-dimensional array of CMUT elements 121. Each element 121 of the array is formed of numerous parallel-connected capacitor cells, forming an array of small capacitor cells. Each capacitor cell has a top electrode (metalized membrane) suspended above a heavily doped silicon substrate that forms the bottom electrode. The membrane supporting the metallic top electrode is separated from the substrate by a vacuum gap. The vacuum gap may be formed in an insulating layer that covers the substrate. Immersive operation is possible for the CMUT since the vacuum gaps beneath the membrane are sealed.

During CMUT operation, a direct current (DC) voltage can be applied between the metalized membrane and the substrate. For example, a common top membrane of the CMUT array (where the membranes of each element form a connected membrane) can be DC biased with a shared off-chip RC network (e.g., RC network 240 shown in FIG. 2B). The biasing current (or voltage) may be supplied through ASIC pins. The membrane is attracted toward the bulk by the electrostatic force of the electric field generated by the application of the DC voltage, while induced stress within the membrane resists the attraction. For a transmit mode, the membrane is driven with an alternating voltage to generate ultrasound. For a receive mode, the membrane is biased by the applied DC voltage and when the biased membrane is subjected to ultrasound, a current output is generated due to the capacitance change under the constant bias voltage. The amplitude of this current output is a function of the frequency of the incident wave, the bias voltage, and the capacitance of the device.

Figures 2A, 2B:
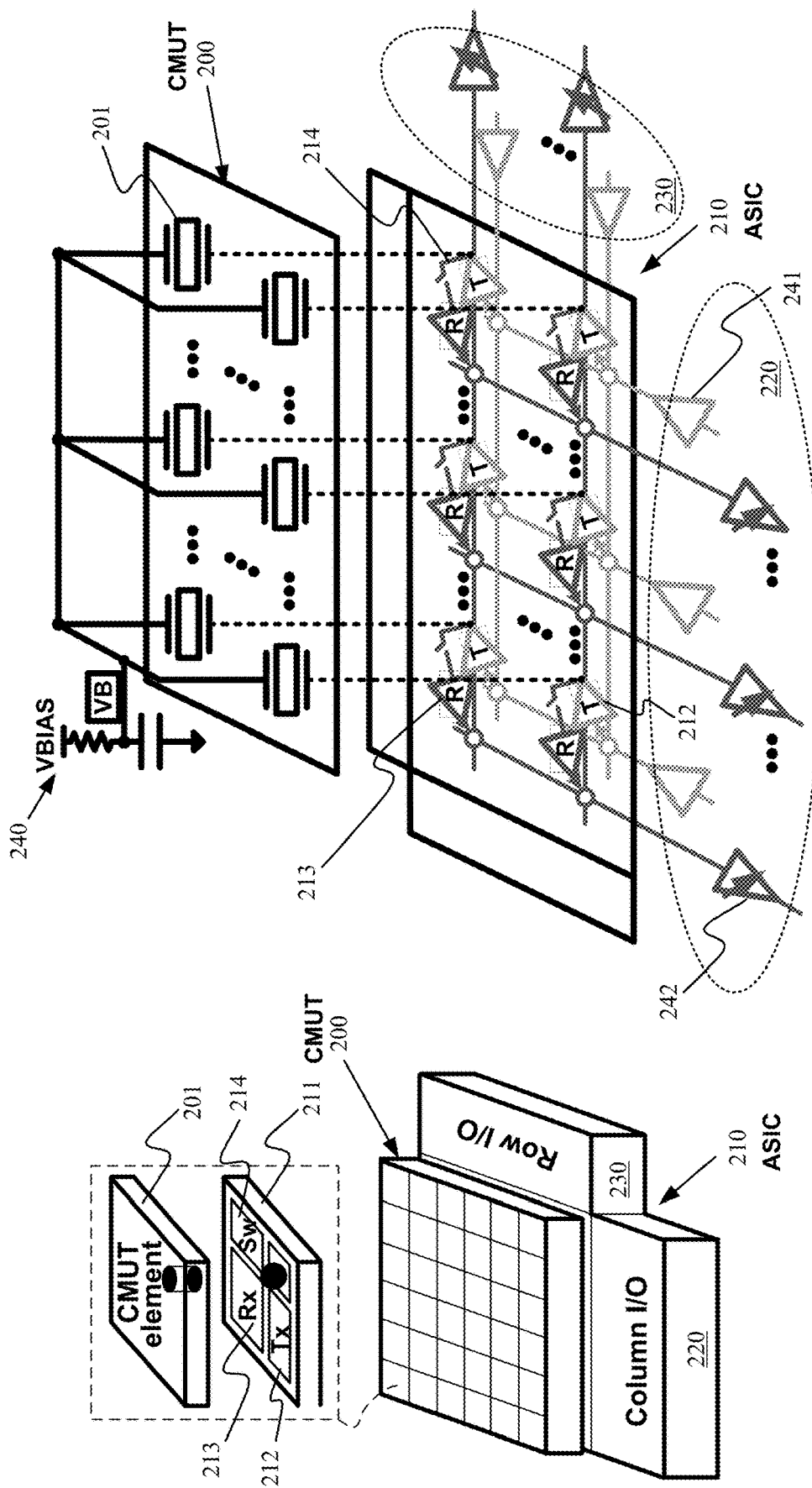
FIG. 2A illustrates an ultrasonic transceiver of a compact ultrasound device.
FIG. 2B shows a schematic representation of the ultrasonic transceiver of FIG. 2A according to an illustrative example.

FIG. 2A illustrates an ultrasonic transceiver of a compact ultrasound device; and FIG. 2B shows a schematic representation of the ultrasonic transceiver of FIG. 2A according to an illustrative example. A column-row-parallel architecture at the circuit level of the ultrasonic transducer enables the transmit and receive modes of a N×M CMUT array (or other transducer array) to be driven by a programmable ASIC column-parallel or row-parallel, independently. The circuit-level column-row-parallel architecture supports a programmable element addressing scheme for various sub-array apertures (see e.g., FIGS. 8A-8F).

As illustrated in FIG. 2A, a CMUT array 200 can be stacked on a programmable ASIC 210 having a column input/output (I/O) logic 220 and row I/O logic 230 (in addition to other elements including row/column/element selection logic such as described with respect to FIG. 1). For implementations involving a CMUT array or other silicon-based chip for the transducer array, the transducer chip can be bonded to the ASIC using any suitable stacking method including, but not limited to, flip-chip stacking with its various bonding materials and methods such as solder or gold bump fusion, adhesion thermo-compression, metal-metal thermo-compression, and hybrid methods. In some cases, interposer layers or substrates may be used.

The CMUT 200 can be DC biased with a shared off-chip RC network 240 such as shown in FIG. 2B. Each element 201 of the 2D CMUT array 200 can be positioned over a corresponding transceiver element 211 of the ASIC 210. Element 201 can have a bottom pad connected to its corresponding ASIC front-end channel (transceiver element 211). The transceiver element 211 can include a transmitter (Tx) pulser circuit 212, a receiver (Rx) low noise amplifier (LNA) 213, and a receiver high voltage (HV) protection switch 214. The silicon area for the transceiver element 211 can be designed to element-match to the CMUT pitch for compact flip-chip bonding assembly through a PCB interposer. Tx pulser drivers 241 and Rx line buffer amplifiers (VGAs) 242 can be placed at the ASIC perimeter to interface to the front-end array as part of the column I/O 220 and row I/O 230. There are N copies of Tx drivers and Rx buffers at the column side and M copies at the row side. The number of ASIC I/Os can be further reduced from the N+M number of I/Os by multiplexing the column and row I/O. For example, where N=M, the number of ASIC I/Os can be reduced to N (see e.g., FIGS. 7A and 7B).

Figure 3A:
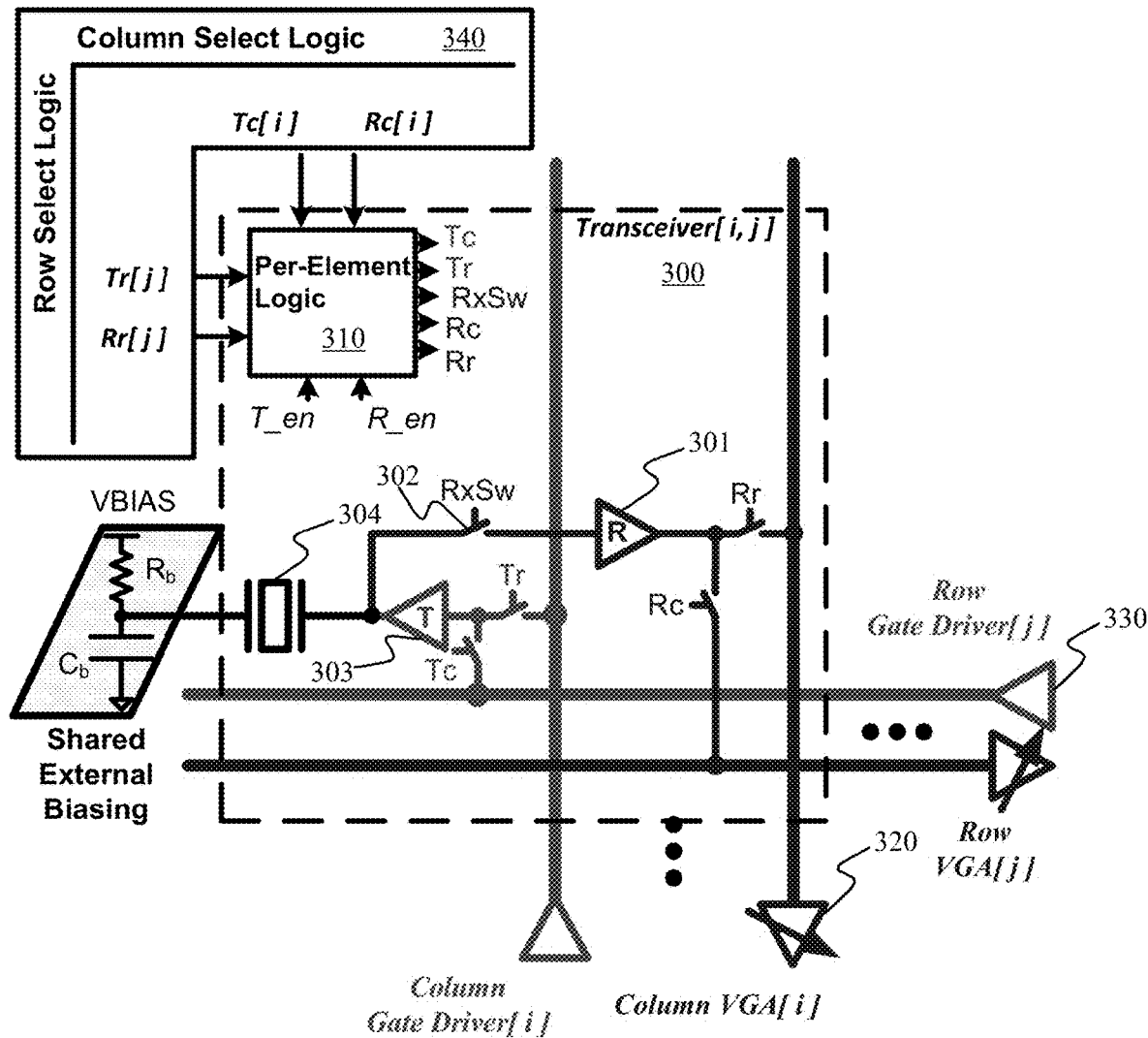
FIG. 3A illustrates a block-level implementation of a single transceiver channel with corresponding transducer.
Figure 3B:
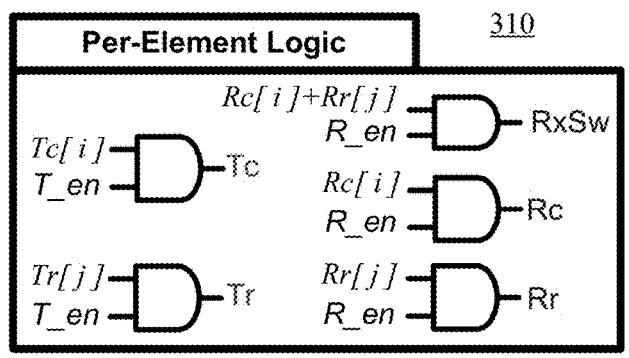
FIG. 3B illustrates a per-element logic implementation.

FIG. 3A illustrates a block-level implementation of a single transceiver channel with corresponding transducer; and FIG. 3B illustrates a per-element logic block implementation. Referring to FIG. 3A, an element 300 located at the i-th column and j-th row (<i, j>) of a N×M column-row-parallel architecture includes a receiver element 301 (LNA) with a receiver high voltage (HV) protection switch 302 and a pulser circuit 303 connected to a transducer element (e.g., CMUT element 304). Each element 300 also includes a per-element logic block 310. The output of the receiver element 301 is connected by switches controlled by signal Rr and signal Rc to a shared column or row buffer 320, which may be located at the periphery of the transceiver array. When the switches do not connect the receiver element 301 to one (or both) of the shared buffers 320, the receiver element can be considered to be turned off. The HV protection switch 302 (controlled by signal RxSw) protects the low voltage (LV) Rx circuit from high voltage (HV) Tx transients. The input to the pulser circuit 303 is driven by a row or gate driver 330 whose output is selectively connected to the pulser circuit 303 by switches controlled by signal Tr and signal Tc. Selection of a row or column is controlled by row and column select logic 340.

Since transmitter mode and receiver mode are independent and similar, the receiver mode can be used as an illustration of an operation of the transceiver channel. In this illustration, the control inputs are: i-th column (Rc[i]) and j-th row (Rd[j]) select signals from the sides; and per-element enable bit (R_en). The resultant local control signals are shown in FIG. 3B. As shown in FIG. 3B for the example implementation of the per-element logic block 310, the per-element logic can include a plurality of AND logic gates, where Tc[i] and T_en are used to provide Tc; Tr[j] and T_en are used to provide Tr, Rc[i]+Rr[j] and R_en are used to provide RxSw; Rc[i] and R_en are used to provide Rc; and Rr[j] and R_en are used to provide Rr. In this manner, the enable bits are used to control whether a particular element on a row and column is selected for activation.

Figure 4A:
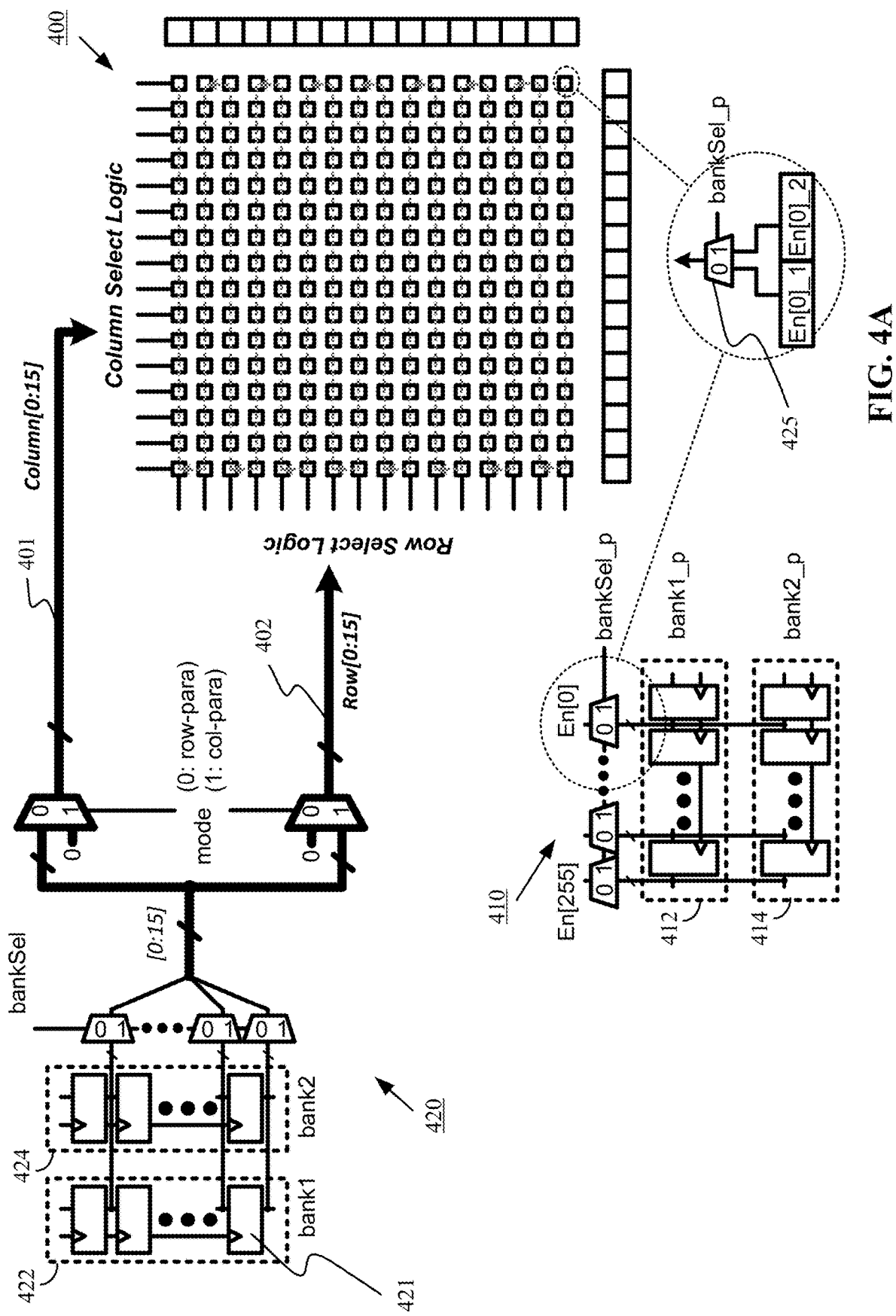
FIG. 4A illustrates control logic for a column-row-parallel ASIC architecture.

FIG. 4A illustrates control logic for a column-row-parallel ASIC architecture. Referring to FIG. 4A, a 2D array of transceivers 400 receive control signals (bits) for column selection 401 (e.g., Tc[i], Rc[i]), row selection 402 (e.g., Tr[j], Rr[j]), and per-element enable 410 (e.g., T_en, R_en). Column and row logic 420 provides the bits for column selection 401 and row selection 402 and can include at least one bank with registers 421 for storing a transmit or receive pattern. In the illustrated example, two banks 422, 424 are included, which in some implementations may be alternatingly selected using a "bankSel" control signal (which may be a clocked signal). For implementations using consolidated row and column select signals (e.g., where N I/O signals are available for the N×N (or N×M where N>M), a set of MUXes can be included as part of the column and row logic 420. A "mode" signal, provided by a controller, can select whether column or row selection is taking place.

The column-row-parallel architecture is both scalable and flexible. The columns and rows are reprogrammable for flexible 3D beam-formation (e.g., the select logic for the columns (column selection 401) and the select logic for the rows (row selection 402) can be reprogrammed quickly and frequently to activate different rows or columns for 3D beamforming); the programming time also scales with N (for example, 0.16 μs by a 100 MHz clock). A pattern to transmit and a pattern to receive can be set for a particular ultrasound mode (the mode having a particular per-element enable pattern). The time to program consecutive transmits is relatively fast since the number of bits is N+M (or N if N=M and a MUX is used). However, the time to program a particular mode (e.g., aperture pattern), can be relatively slower since each element of the N×M array has an associated bit (or two).

Per-element enable 410 provides the bits for each element of the array 400 and can also include at least one bank 412, 414 for storing an enable pattern that programs a snake-chain of shift registers 425. Per-element enable bits are programmed by the snake-chained shift registers 425 through the array 400, which offer fine granularity for application-specific patterns, making the described column-row-parallel ASIC architecture compatible with existing beamforming schemes such as described in S. Smith et al., "High-speed ultrasound volumetric imaging system. i. transducer design and beam steering," *IEEE UFFC*, 1991; M. Karaman et al., "Minimally redundant 2-d array designs for 3-d medical ultrasound imaging," *Medical Imaging, IEEE Trans. on,* 2009; B.-H. Kim et al., "Hybrid volume beamforming for 3-d ultrasound imaging using 2-d CMUT arrays," in *IEEE Ultrasonics Symposium,* 2012; C. H. Seo and J. Yen, "A 256×256 2-d array transducer with row-column addressing for 3-d rectilinear imaging," IEEE UFFC, 2009; M. Rasmussen et al., "3-d ultrasound imaging performance of a two-column addressed 2-d array transducer: A measurement study," IUS'13; and A. Savoia et al., "Crisscross 2d CMUT array: Beamforming strategy and synthetic 3d imaging results," in IEEE Ultrasonics Symposium, 2007, while enabling new patterns including checkerboard and annular rings (see FIGS. 8A-8F, 16, 18A-18F, and 19A-19F).

Figure 4C:
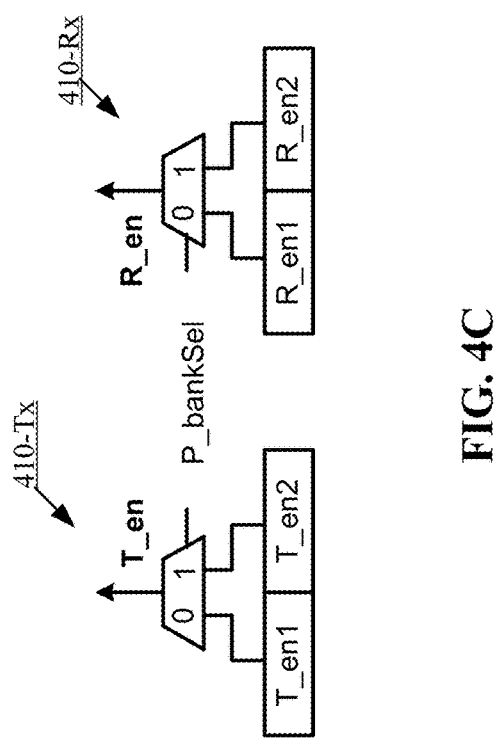
FIGS. 4B and 4C show additional detail for the control logic of FIG. 4A.
Figure 4B:
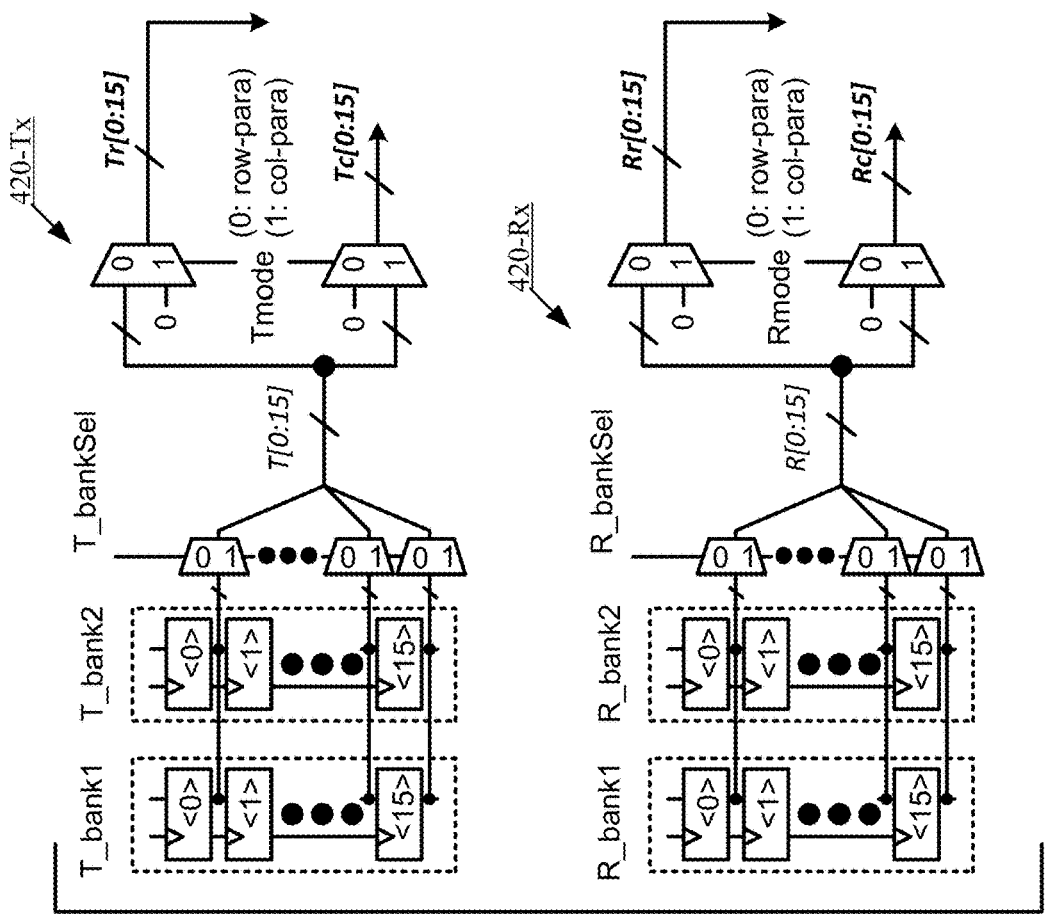

For column and row logic 420 and Per-element enables 410, there are two identical copies for the Tx and Rx controls, as illustrated by the Tx column and row logic 420-Tx and Rx column and row logic 420-Rx of FIG. 4B and the Tx per-element enable 410-Tx and Rx per-element enable 410-Rx of FIG. 4C.

The pre-programmed shift register bank (one or more of 412, 414 422, 424) can be used to enable fast application of a specific pattern after loading the pattern into the bank. For faster operation, each control set (column, row, per-element) has two multiplexed (e.g., using "bankSel" and "bank-Sel_p") shift register banks (412 and 414 for per-element enable 410; 422 and 424 for column and row logic 420) to allow operation based on one bank while reprogramming the other; or alternating two pre-programmed banks for fast imaging aperture switching. For example, "If (SEL=1), R_en=Rbank1; else, R_en=Rbank2". The two-bank approach allows operation based on one bank while reprogramming the other; or alternating two pre-programmed banks for fast imaging aperture switching.

Advantageously, it is possible to activate the imaging system at the definition of per-element to form arbitrary transmit or receive apertures. In certain implementations, it is possible to parallelize several transmit channels to increase acoustic power delivery and increase effective transmit aperture size. Similarly, in certain implementations, it is possible to parallelize several receive channels to improve signal to noise ratio and increase effective receive aperture size.

A fault-tolerance component can further be included to improve assembly yield and test speed as CMUTs, or other types of 2D transducers, scale to higher spatial resolution. In the illustrated implementation, the per-element enable bits introduce fault tolerance against defective shorting CMUT elements in the array.

Figure 5B:
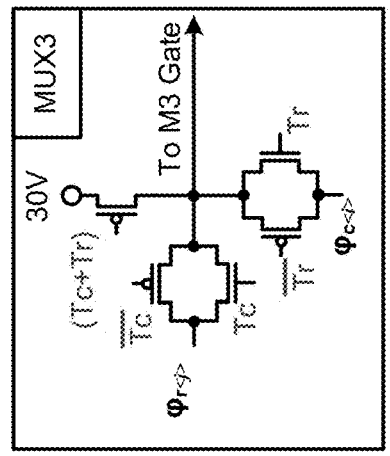
FIG. 5B shows a detailed view of the MUX3 of FIG. 5A.
Figure 5A:
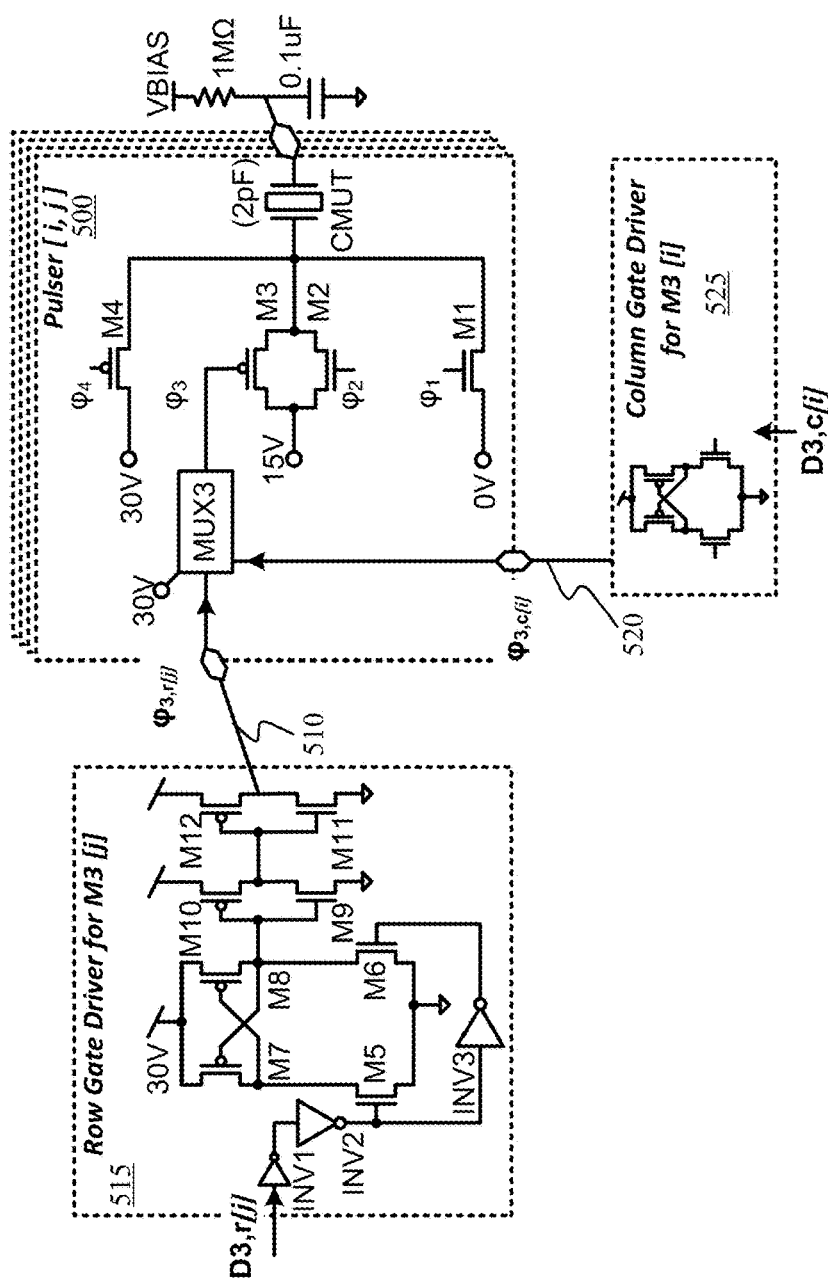
FIG. 5A illustrates a specific implementation of a pulser for a column-row-parallel ASIC architecture.

FIG. 5A illustrates a specific implementation of a pulser for a column-row-parallel ASIC architecture, for example, for a row or column of transmitter pulser circuits 212, 303 and a shared pulser gate driver 241, 330 of FIGS. 2B and 3A. Referring to FIG. 5A, a three-level 30 Vpp pulse shaping pulser can be used for each transmitter pulser circuit 500.

As shown in FIG. 5B, high voltage pass-gate MUXes implement Tr and Tc inside each 3-level 30 Vpp pulse-shaping pulser. If the pulser is off, the MUX3 sends a "hold" voltage to pulser gate M3, ignoring column and row drivers. The 2D grid of column and row lines uses minimum width metal wires for least parasitic capacitance. When multiple pulsers 500 on one line (510, 520) are driven by the same driver (515, 525), their CMUT elements' acoustic outputs combine in space. These elements are effectively in parallel and behave as a larger CMUT element with bigger acoustic energy output.

Figure 6A:
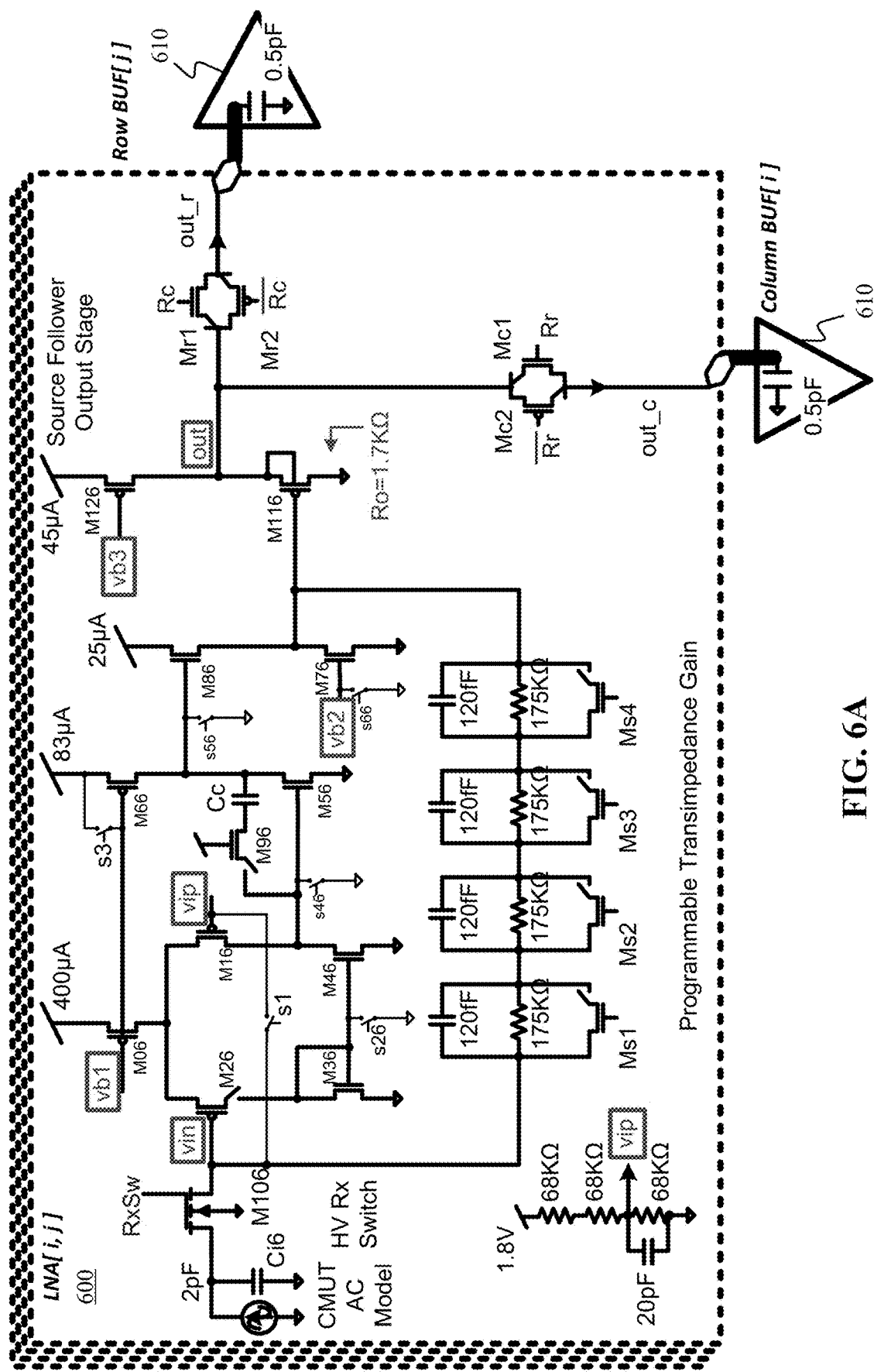
FIGS. 6A-6G illustrate various implementations for a receiver and related components for a column-row-parallel ASIC architecture.
Figure 6B:
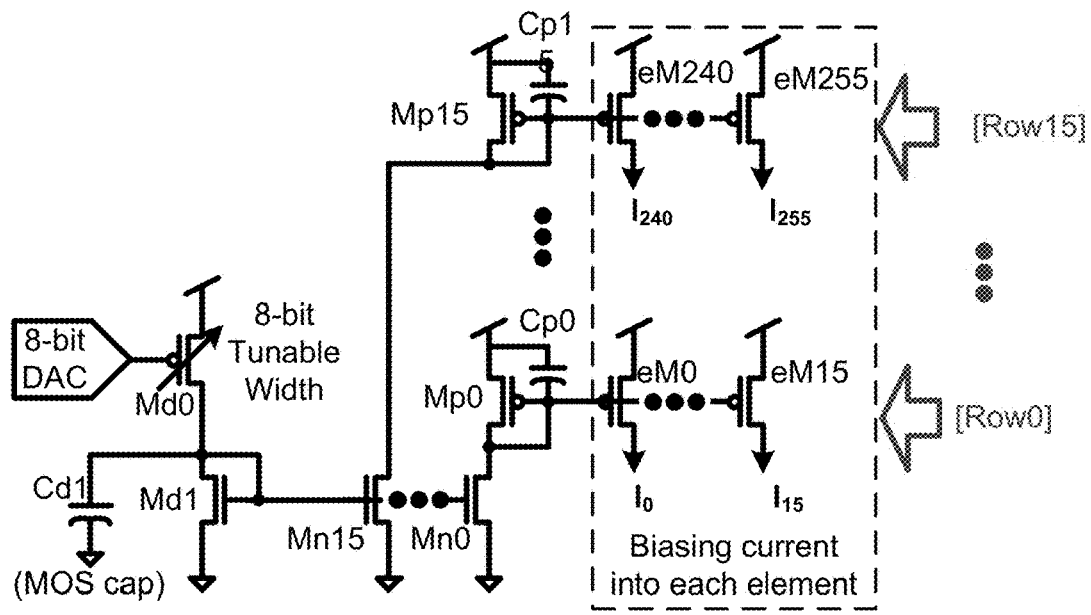

FIG. 6A shows a schematic of an LNA 600 at [i,j] with a row buffer amplifier at j-th row (the column buffer at i-th column is not shown). FIG. 6B is a schematic of a current biasing scheme for the array of receiver amplifiers (e.g., the array of LNAs 600) in a column-row-parallel ASIC architecture For Rx, LNA outputs on the same line can be combined (and input to a VGA 610) such that signals are averaged and noise is reduced, effectively achieving parallelism as if receiving from a larger CMUT element with multiple parallel LNAs. As shown in FIG. 6A, a source follower stage (M11-M12) is used to provide a suitable LNA output impedance (Ro) for analog combining. However, it should be understood that the source-follower configuration is only one possible implementation for parallelism and other configurations may be used to implement the parallelism for the lines.

Returning to FIG. 6A, Ro is selected to be high enough to allow current summing. Otherwise device mismatch and line resistance (Rp) will disturb the DC condition and distort signals when parallelizing. Ro is also selected to be low enough to ensure single LNA's performance. Otherwise the bias current (Io) may be too low to maintain good output linearity; and the line capacitance (Cp) limits the bandwidth. The design starts with a slew constraint to fix Io>34 µA with Ro<2.2 kΩ. Then 10× minimum width metal wires are chosen to provide Rp<<Ro for current summing. Simulations were performed and results are shown in Table I.

TABLE I

|  | 2x | 4x | 8x | 16x |
| --- | --- | --- | --- | --- |
| Theory (dB) | 3 | 6 | 9 | 12 |
| Measured (dB) | 2.41 | 5.41 | 8.20 | 10.86 |

Table I shows that measured SNR increase with parallel LNAs is close to theory; the discrepancy is likely due to correlated noise sources. Other measured results are in Table II.

TABLE II

| | | |
| --- | --- | --- |
| R | Power | 1.4 mW |
| x | Sleep Power | 0.054 mW |
| | Bandwidth | 10.2 MHz |
| | Noise | 2.3 mPa/√Hz@5 MHz |
| | Rx Sensitivity | 7.3 mPa(rms) |
| | Rx Responsivity | 123 mV/kPa |
| | Gain | 116/113.5/110/104 dBΩ |
| | Gain Mismatch | <2.0 dBΩ (over 256 channels) |
| | Crosstalk | <−50 dBc@3 MHz; <−22 dBc@15 MHz |
| | Po1dB | 946 mVpp |
| | HD2 | −46 dBc@330 mVpp, 2 MHz tone |
| | IMD3 | −72 dBc@324 mVpp, 2&2.01 MHz tone |

TABLE II-continued

| T | Active Power | 7.1 mW @ 4.2 MHz |
| x | Min Pulse Width/Bandwidth | 20 ns/50 MHz |

The Rx LNA implementation shown in FIG. 6A exhibits a linear output stage and a low power sleep mode. This design provides programmable gain, greatly enhancing system flexibility.

As can be seen from Table I, the measured channel SNR improvement deviates from the theoretical expectation more as the channel parallelism increases. The performance degradation is the result of the line parasitics and indicates that the parallelism cannot be scaled up to infinite number of channels. According to the numbers shown in Table I, it is expected that it will not be possible to maintain a satisfactory bandwidth performance for the channel located at the farthest end of the line when the line length is excessively long.

However, there are several techniques that may be used to mitigate the negative effect from the line parasitics and improve the scaling to an even larger array (e.g., an array larger than 256×256). The following examples may be used alone or in combination to minimize the negative effects of the line parasitics.

As one example, the source follower stage bias current and transistor sizing can be increased to enable more than 16× parallel channels with the same performance. The corresponding line width would be increased approximately proportionally to keep Rp<<Ro for current summing. Channel count increase in this way will stop when a self-loading condition for circuit bandwidth is reached. At that point, Cp becomes the dominant load at the output, and the increase of Cp offsets the reduction of Ro. Circuit simulation shows that at around 64× parallelism with a 40× minimum metal line width, self-loading is reached; increasing output stage sizing and power consumption does not extend parallel channels any more.

The metal wire layout for the example ASIC implementation is using only one layer of metal. Thus, another example to reduce parasitics includes several metal layers that are connected in parallel to yield a better line parasitics model. For example, by using two metal layers in parallel to implement the interconnecting column and row lines, Rp is reduced by 2× while Cp is increased by a factor that is much less than 2×, because there are no coupling capacitance between the two metal layers at the same potential. As a result, the channel parallelism can be approximately extended further by close to 2×.

As yet another example, the column or row lines can be interconnected from both ends to the column or row buffers, effectively reducing the line parasitics. The worst case channel in this scenario becomes the one at the center of a line, rather than the ones at the two ends. Therefore, approximately another 2× more channels can be placed in parallel with the same performance.

Figure 6C:
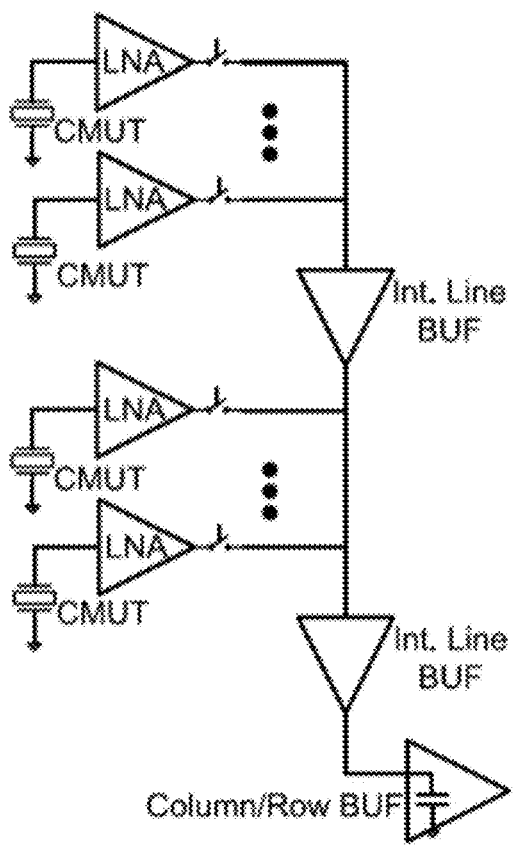

Lastly, as another example, inserting intermediate buffering stages in the middle of interconnection lines could extend the number of parallel channels even further, as shown in FIG. 6C. Within each intermediate block, 16-64× channel outputs can be combined in parallel by each channel's buffer stage. The additional line buffers inserted could attain parallelism with even more channels without excessive bandwidth/linearity performance degradation.

FIGS. 6D-6G illustrate implementations of a VGA with automatic offset cancelation. The input to a shared column or row VGA is not fixed due to the various configurations available for the aperture where not all of the LNAs of a particular row or column will be connected to that particular row's or column's shared VGA. Because, in some cases, there may be too many channels for effective manual tuning, a VGA with offset cancelation is presented. The VGA is suitable for the column-row-parallel architecture as well as other applications where there is a varied load or input.

Figure 6D:
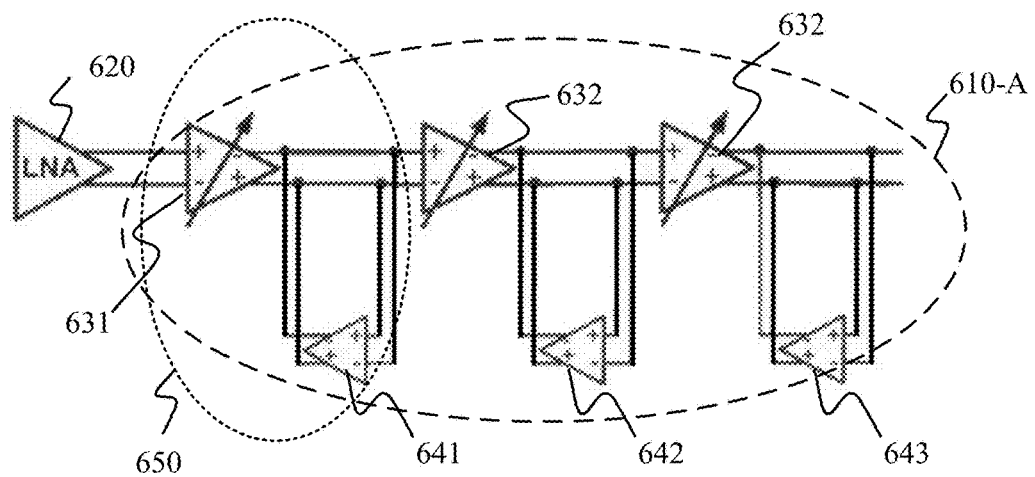
Figure 6E:
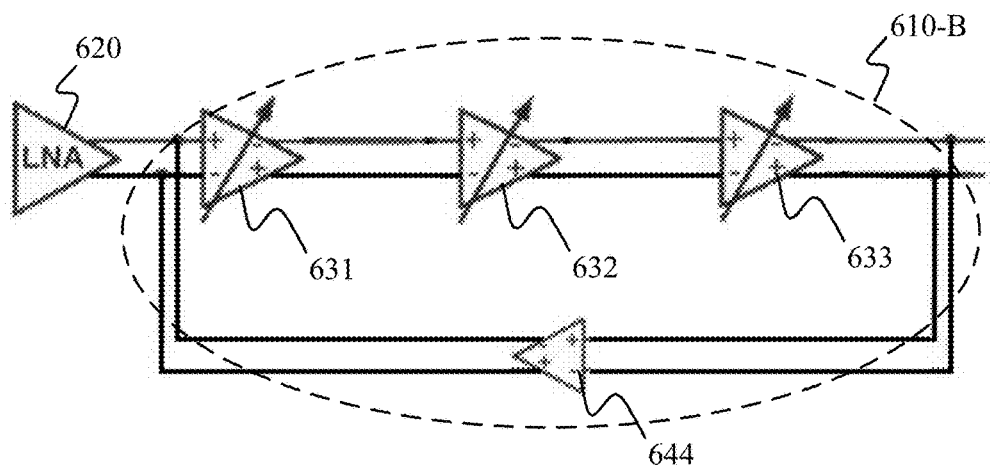

As illustrated in FIGS. 6D and 6E, a VGA 610-A, 610-B (for VGA 610 of FIG. 6A) receives an output of a variable number of LNAs 620 (which may be implemented as LNA 600 of FIG. 6A). The illustrated VGAs 610-A, 610-B include three differential amplifiers 631, 632, 633; however embodiments are not limited to three differential amplifiers (more or less may be suitable in certain implementations). To perform the automatic offset cancelation, a loop is included at the column or row side that automatically cancels offsets coming from the LNA 620. The loop includes a feedback buffer, for example a differential amplifier. After the LNA receivers 620 are combined, the output is buffered by the shared VGA 610-A, 610-B, which includes the three differential amplifiers 631, 632, 633. Offsets are random and might saturate the amplifiers if not corrected. The inclusion of a loop in the VGA inhibits saturation.

Figure 6F:
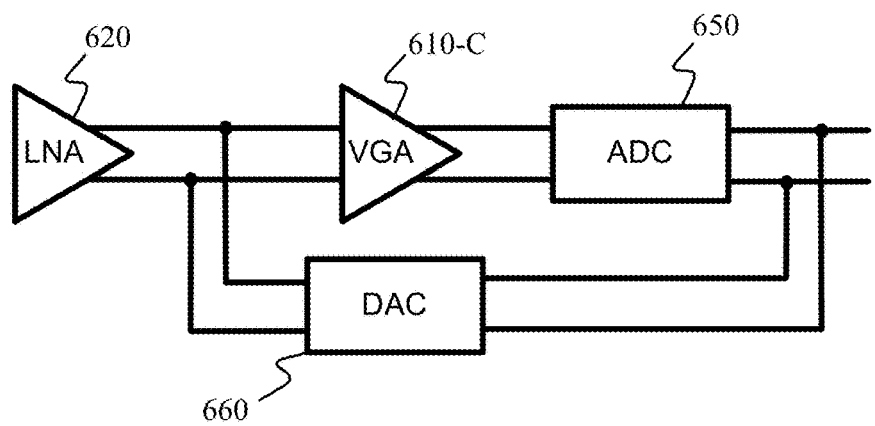
Figure 6G:
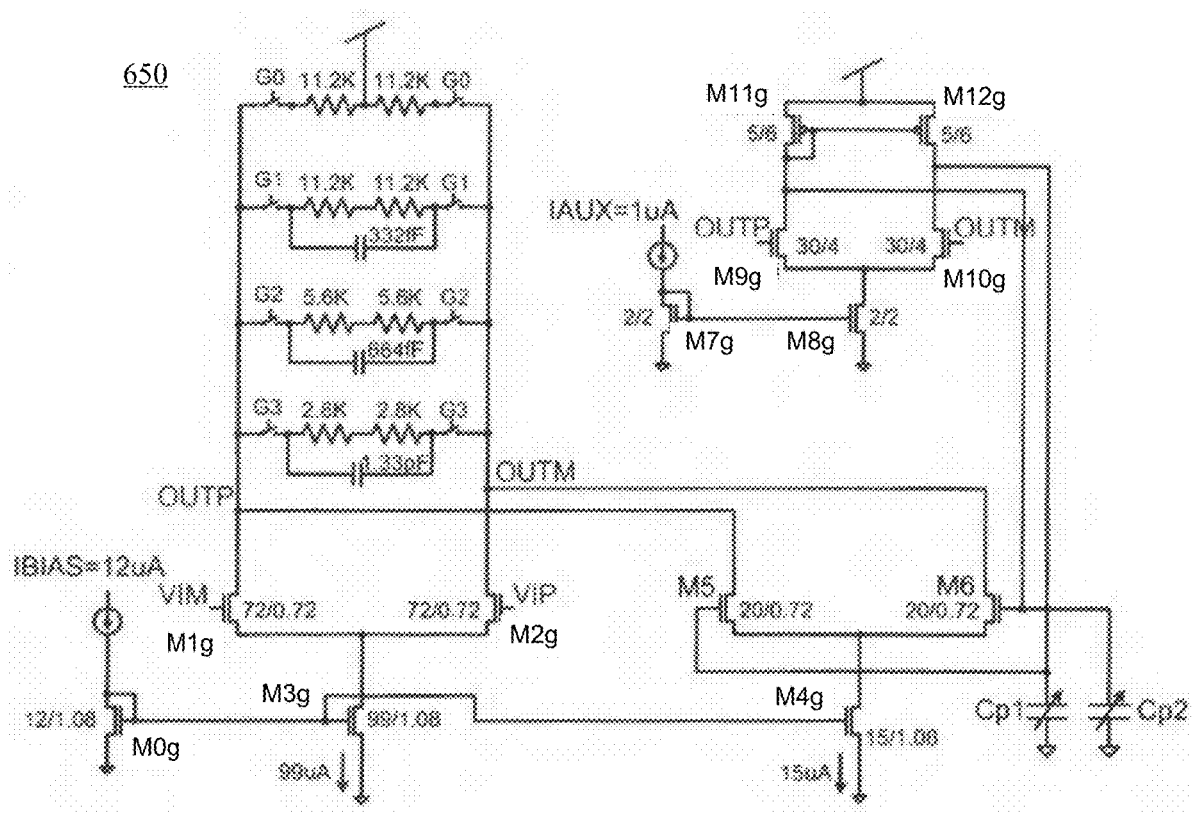

In FIG. 6D, each differential amplifier 631, 632, 633 has a corresponding cancelation loop 641, 642, 643 at its output; whereas in FIG. 6E, a single loop 644 going from the end of line of differential amplifiers 631, 632, and 633 is fed back to the output of the LNA 620 (where the LNAs all connect even when they are not activated). Other configurations and combinations of the cancelation loops and numbers of differential amplifiers are contemplated. For example, as illustrated in FIG. 6F a mixed-signal cancelation loop can be formed by first digitizing the analog signal output of the VGA 610-C using an analog-to-digital converter (ADC) 650, and then feeding back the digital signal to the output of the LNA 620 through a digital-to-analog converter (DAC) 660. FIG. 6G shows a schematic representation of one differential amplifier and cancelation loop stage 650.

Figure 7B:
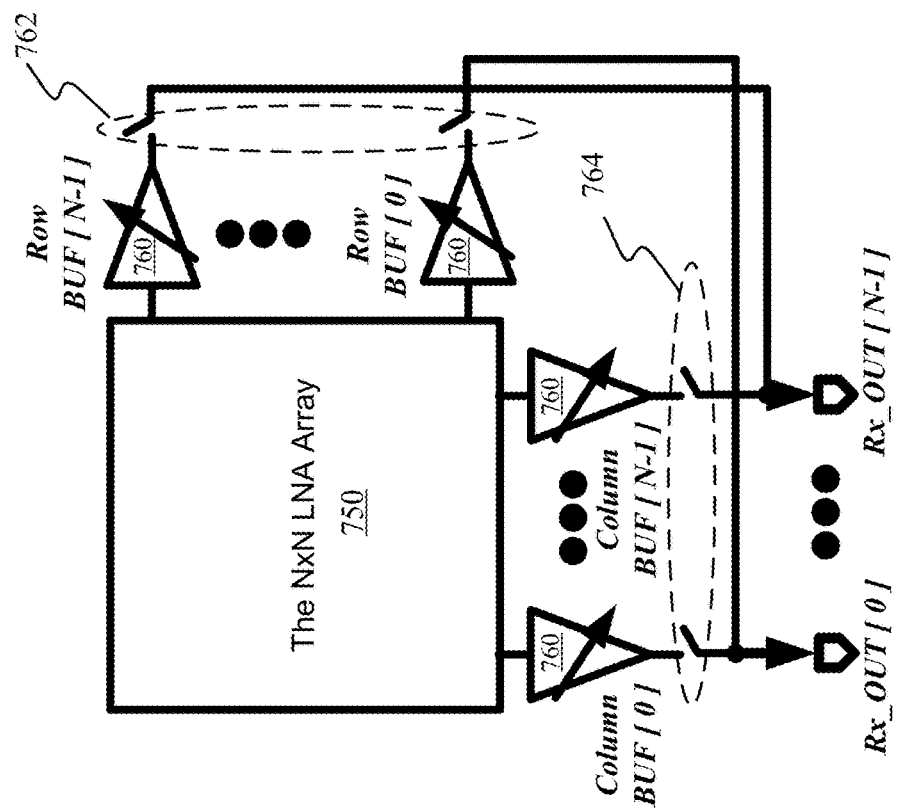
FIGS. 7A and 7B illustrate a multiplexing arrangement for the transmitter (FIG. 7A) and receiver (FIG. 7B) column and row input/output (I/O) of a column-row-parallel architecture having a N×N array.
Figure 7A:
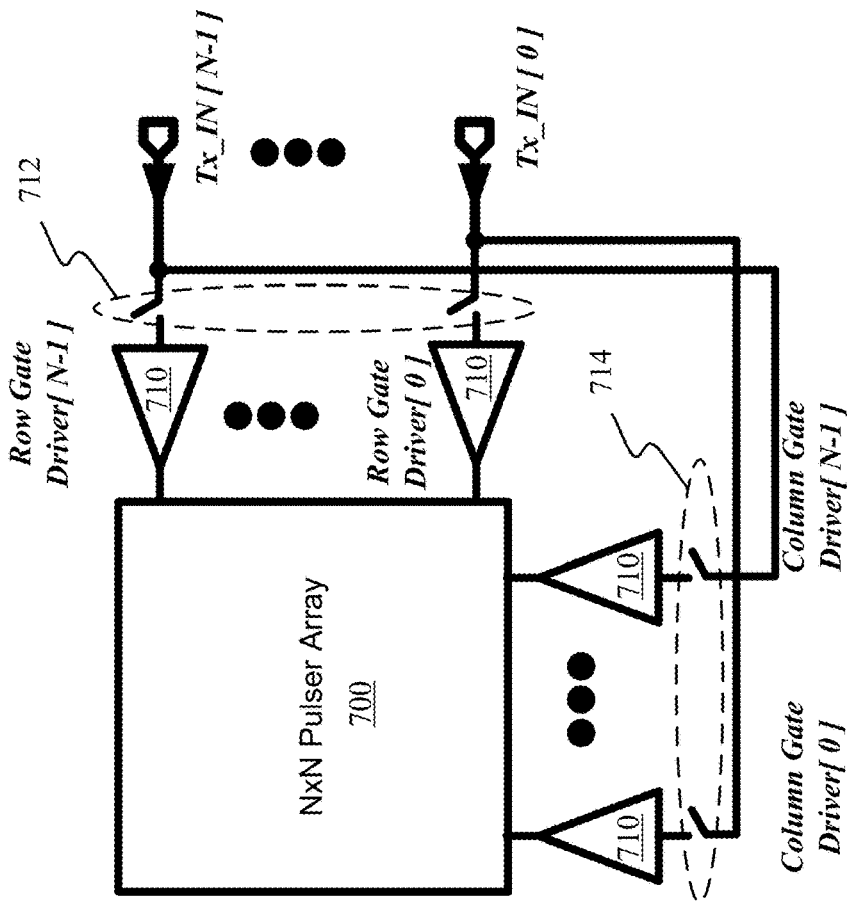

FIGS. 7A and 7B illustrate a multiplexing arrangement for the transmitter (FIG. 7A) and receiver (FIG. 7B) column and row input/output (I/O) of a column-row-parallel architecture having a N×N array. Referring to FIG. 7A, the transmitter circuitry includes a N×N pulser array 700 and a gate driver 710 for each row and column of the N×N array. Here, N row gate drivers (Row Gate Driver[0] to Row Gate Driver[N-1]) and N column gate drivers (Column Gate Driver[0] to Column Gate Driver[N-1]) are included. Instead of a total of 2N inputs to the ASIC needed to drive the N×N pulser array 700, a total of N inputs (Tx_IN [0] to Tx_IN [N-1]) can be used by incorporating row switches 712 and column switches 714 controlled by a MUX (not shown) that selects column or row.

Referring to FIG. 7B, the receiver circuitry includes a N×N LNA array 750 and a buffer 760 (e.g., VGA) for each row and column of the N×N array. Here, N row buffers 760 (Row BUF[0] to Row BUF[N-1]) and N column buffers (Column BUF[0] to Column BUF[N-1]) are included. Instead of a total of 2N inputs to the ASIC needed to output the N×N LNA array 750, a total of N outputs (Rx_OUT [0] to Rx_OUT [N-1]) can be used by incorporating row switches 762 and column switches 764 controlled by a MUX (not shown) that selects column or row. The input and output lines may share pins/ports when logic is included to differentiate between transmit and receive mode.

The described column-row-parallel ASIC architecture enables various programmable apertures, using a column-parallel or row-parallel mode that is controlled by a combination of row select, column select, and per-element enabling logic. FIGS. 8A-8F illustrate example apertures that may be implemented using the described architecture.

Figure 8A:
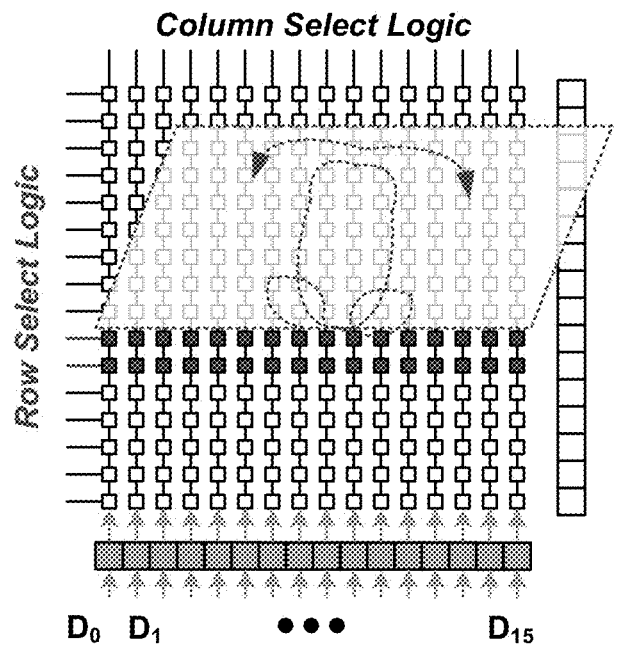
FIGS. 8A-8F illustrate example apertures that may be implemented using the described architecture.
Figure 8B:
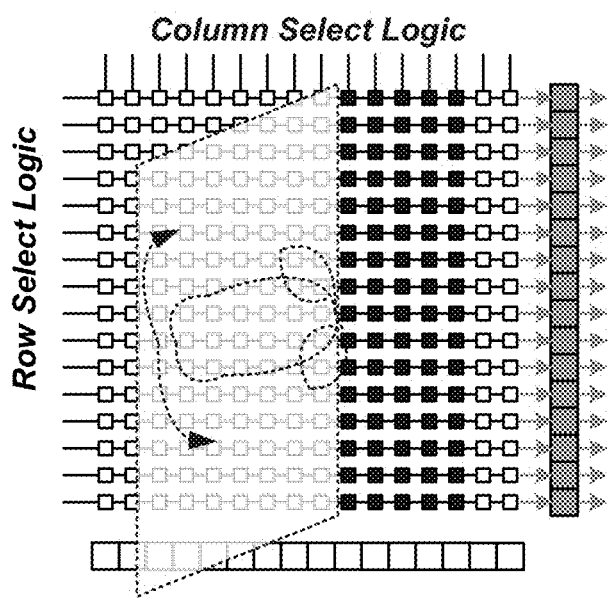

In column-parallel mode, the column circuitry is active while the row select logic determines which elements are parallelized along each column. For example, in FIG. 8A, two Tx elements are activated in parallel for each column, driven by a shared column driver. Tx azimuth beam-formation is realized by applying relative delays to the column drivers (e.g., $D_0, D_1, \ldots D_{15}$). In row-parallel mode, the row circuitry and the column select logic are active. For example, in FIG. 8B, an Rx aperture in row-parallel mode can be implemented by activating the row circuitry and the column select logic. In FIG. 8B, five active Rx channels along the same row are in parallel. The signals of the five active Rx channels are averaged and output by the row buffer. In some cases, the output of the channels can be to external analog-to-digital converters (ADC). Rx elevation beamformation is implemented with delay and summed across all the row signals after digitization. The beamforming illustrated in FIGS. 8A and 8B can be realized by applying relative delays to the column or row Tx drivers in real-time and the column or row Rx buffers in post-processing.

Figure 8C:
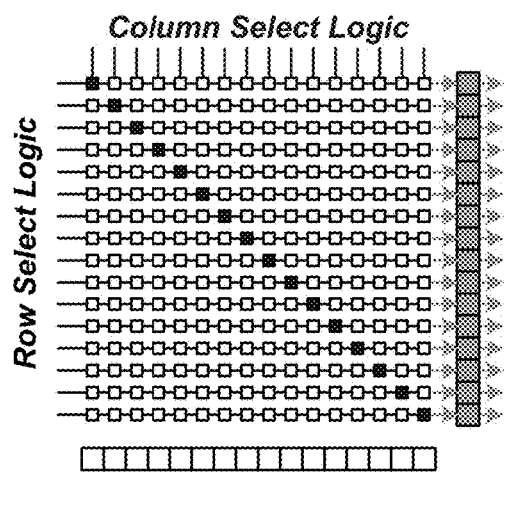
Figure 8D:
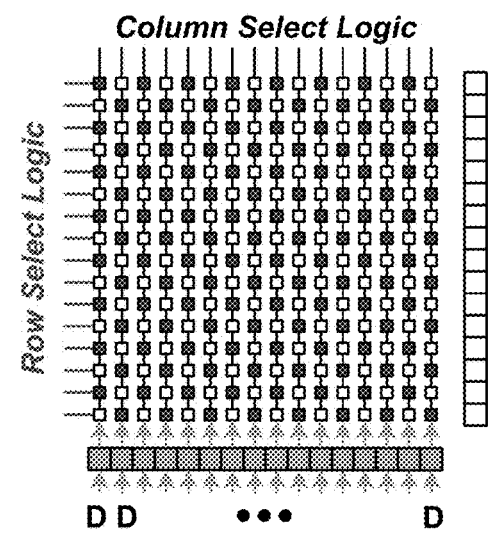
Figure 8E:
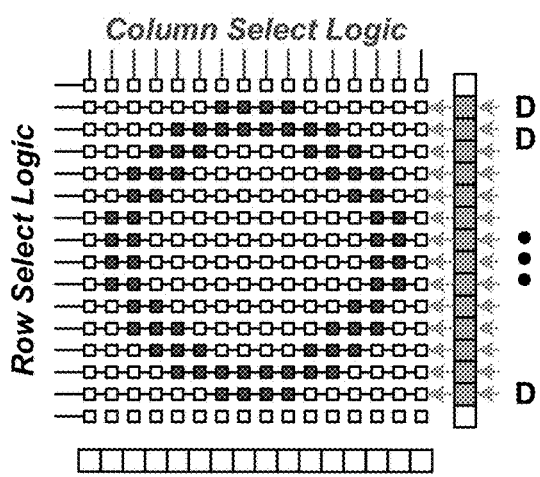
Figure 8F:
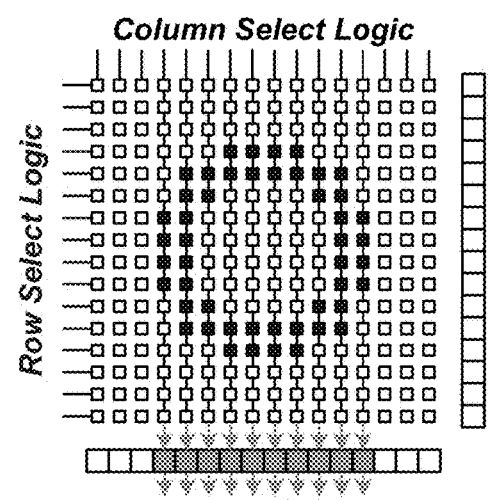

In addition to row-by-row or column-by-column operations, more complex aperture patterns are possible with the use of per-element enable bits in each frontend channel. The intersection of selected rows/columns and asserted individual channels defines the active aperture. FIG. 8C shows an example of a Tx checker board, FIG. 8D shows an example of an Rx diagonal aperture, and FIGS. 8E and 8F show examples of annular ring apertures (FIG. 8E shows a Tx mode driven in phase by row gate drivers and FIG. 8F shows an Rx mode annular ring aperture received by column buffers with their outputs digitally combined in phase).

Advantageously annular and beam steering can be conducted in multiple dimensions (e.g., x and y). Since an ultrasonic device formed of the described column-row-parallel architecture can beam-steer in both the X dimension and the Y dimension, plane wave coherent compounding is possible. In addition, a wide spectrum from full plane waves to narrow plane waves may be used. Note that Tx and Rx apertures are independent; each can be put in either column- or row-parallel mode. In addition, the Tx and Rx apertures are time-multiplexed. The number of active rows or columns is also programmable.

Example—Fault Tolerant ASIC Design

Bad elements of a CMUT array or other types of transducer array can be determined through initial testing. Once the bad elements are determined, the location of the bad elements can be stored and/or the bad elements can be marked as having fault. The marked elements can then be disabled. A per-element enable bit lets each element be activated one-by-one to isolate a bad element. MEMS CMUT transducers sometimes suffer from defects. Failure mechanisms include individual shorted elements and individual open elements. The problematic elements are randomly distributed in the array, and their positions vary from device to device. For short elements, the short behavior is also observed to be related to the bias voltage. A higher VBIAS tends to create more short elements; when VBIAS is reduced, some elements that were shorted might turn into a normal element. Fault-tolerant transceivers can be used to successfully deal with the non-functional CMUT elements and easily accommodate the location changes of faulty elements over time or over VBIAS changes.

For the non-functional elements in the array, the open elements do not require special treatment. The transceiver channel with an open element is not useful, since no ultrasonic signal can be emitted or received. The open element does not affect the transceiver circuit, nor prevent other elements from working properly. However, short elements may cause problems. Because the whole 2D array is biased with a shared high voltage supply VBIAS, a short element could propagate the high voltage to the side that is connected to the circuit, exposing the transceiver circuitry under VBIAS and potentially damaging the circuit. Furthermore, if the transceiver circuit provides a relatively low impedance path to ground, VBIAS could be pulled down to close to 0V, sinking current through the low-impedance path from VBIAS to ground. Since VBIAS is shared across the array, the whole array may be insufficiently biased in this situation and become useless.

Therefore, identifying shorts in the CMUT array and removing the short elements is useful in order to continue to use CMUT arrays that have defects. Instead of probing the elements in a 2D CMUT array to identify all the short elements under a certain VBIAS and removing the solder bumps at the positions corresponding to the short elements to prevent the electrical contact between the short CMUT element and the interposer PCB, circuit techniques are used to electrically remove a faulty CMUT element.

Using a probe station to sweep through all the elements of a CMUT array (e.g., 256 elements for a 16×16 array) to find shorts is a very slow and manual process which can be prone to errors. In addition, because each CMUT device has a unique pattern of short elements, it is not an easily automated process to remove the detected shorts. For example, it has been observed that new CMUT short elements might emerge when a different VBIAS voltage is applied. Therefore, a fixed solder ball removal pattern might work at the beginning, but as soon as one single additional new short element emerges, the assembly becomes not usable.

According to certain implementations of the described ultrasound device with CMUT array and column-row-parallel ASIC architecture, the ASIC itself can be used as a scanner and a selector to implement a programmable "channel removal" electrically. The ASIC can both detect and isolate the short elements. FIG. 9A illustrates an example implementation in which instead of using additional circuitry, the front-end high voltage transistors in the transmitter pulser and the receiver switch are arranged so that in each channel, five front-end HV transistors M1, M2, M3, M4 and M10 are directly connected to the CMUT element. M1-M4 are pulser transistors and M10 is the Rx protection switch (RxSw). Their gate voltages can be controlled independently. When all transistors are switched off, the CMUT element is effectively disconnected and "selectively removed" from the array.

To detect short elements, M1 is used to provide a ground path to CMUT, while other four transistors are kept off (illustrated by the "X" in FIG. 9A). The effective circuit connection of all 256 channels of the 16×16 CMUT array of the example implementation (based on the ground path provided by M1) is shown in FIG. 9B. M1 from each channel is sequentially turned on and off, applying a voltage sequence of 0→30→0V to M1's gate. For example, when M1 from channel [0] is on with its gate voltage G1·[0] at 30V, the CMUT in channel [0] is connected across the ground and VBIAS. Normally, the CMUT is a capacitor at DC and the current monitored by the voltage meter is zero.

However, if the CMUT is shorted, the 10 kΩ probing resistor would expose a leakage current through the abnormal CMUT, indicating a short element.

The per-element enable bits in the Column-Row-Parallel architecture can be used to ensure the selective enabling of transceiver channels to only make electrical connections to normal elements. This independent control over each channel permits identification of individual short elements. By iterating through each of the 256 channels, all short CMUT elements can be identified. The ASIC is then programmed such that only the channels with normal CMUTs are enabled, which contribute to the imaging operations. All transceiver channels facing shorted elements can have their front-end HV transistors cut-off during all operations. If new short elements emerge in the device over time, the ASIC can be programmed again to easily account for the changes. FIGS. 9C and 9D illustrate two example assemblies with the short elements marked with a box (e.g., elements 39, 42, 43, and 63 in FIG. 9C; elements 25, 34, 36, 40, 56, 162, 176, 200, 207, and 232 in FIG. 9D).

In this implementation, the maximum acceptable VBIAS is limited to the maximum rated voltage that the HV transistors can withstand. The HV transistors are stressed by the voltage difference between the drain and source; the maximum voltage difference is VBIAS. In the example implementation, the rated maximum |Vds|, |Vgs| of HV transistors are 32V. VBIAS as high as 40V has been applied without breaking the ASIC. A VBIAS of 30V can be used since it already offers enough acoustic pressure and sensitivity to perform the imaging experiments. Advantageously, no repetitive manual device characterization is necessary; and interpolation may be used to make up for any missing elements' signals in digital post-processing.

Example—Prototype

A 16×16 silicon-on-insulator (SOI) CMUT was stacked on an ASIC (0.18 μm high voltage CMOS process) having the column-row-parallel architecture such as described with respect to FIGS. 2A and 2B. The CMUT and ASIC chips were both flip-chip bonded through an interposer PCB. Each CMUT element and its ASIC transceiver (a Tx pulser and a Rx LNA) have the same size of 250×250 μm², while at the ASIC perimeter, 16 column and 16 row pulser gate drivers and buffer amplifiers interface to the transceiver array. The I/Os are multiplexed to share 16 input and 16 output ports, reducing the number of ASIC I/Os to correspond to the number of rows or columns. The CMUT was biased at 20-40 V (VB) using a shared off-chip RC network.

Although a 16×16 array is described in the examples, it should be understood that other array sizes may be implemented, for example 128×128 or 64×128.

Figure 10A:
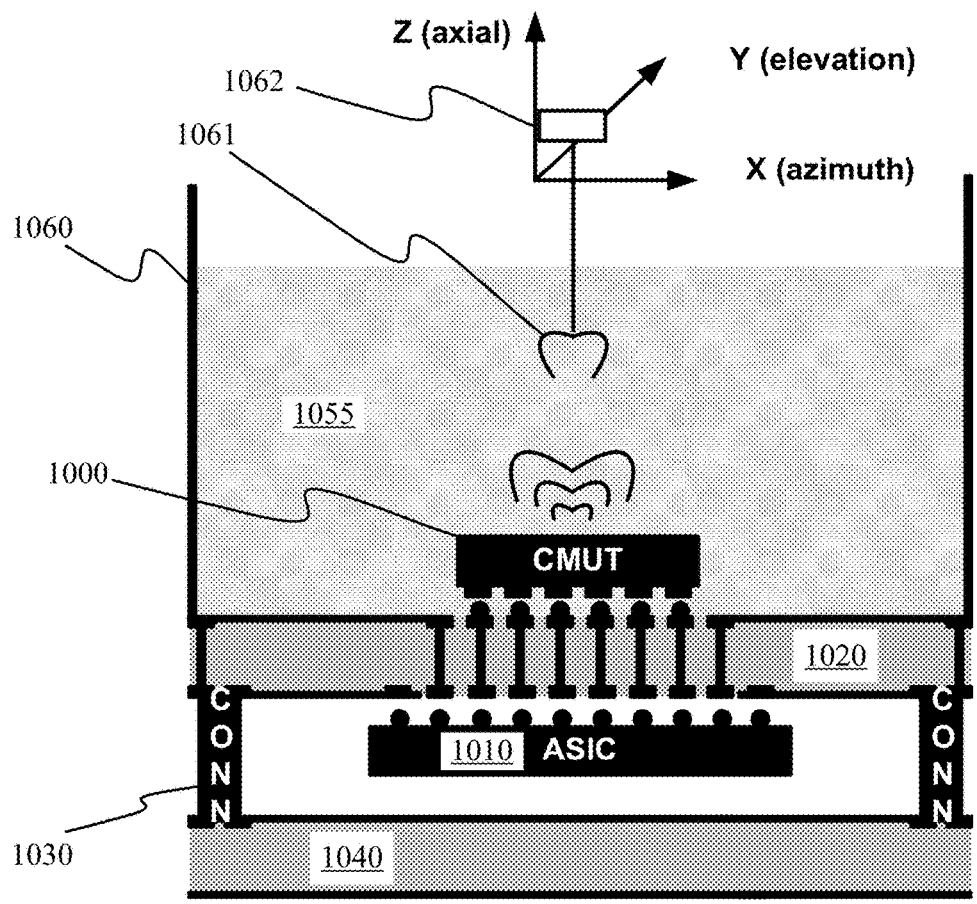
FIG. 10A illustrates a CMUT-ASIC prototype system used in certain experiment examples.
Figure 10B:
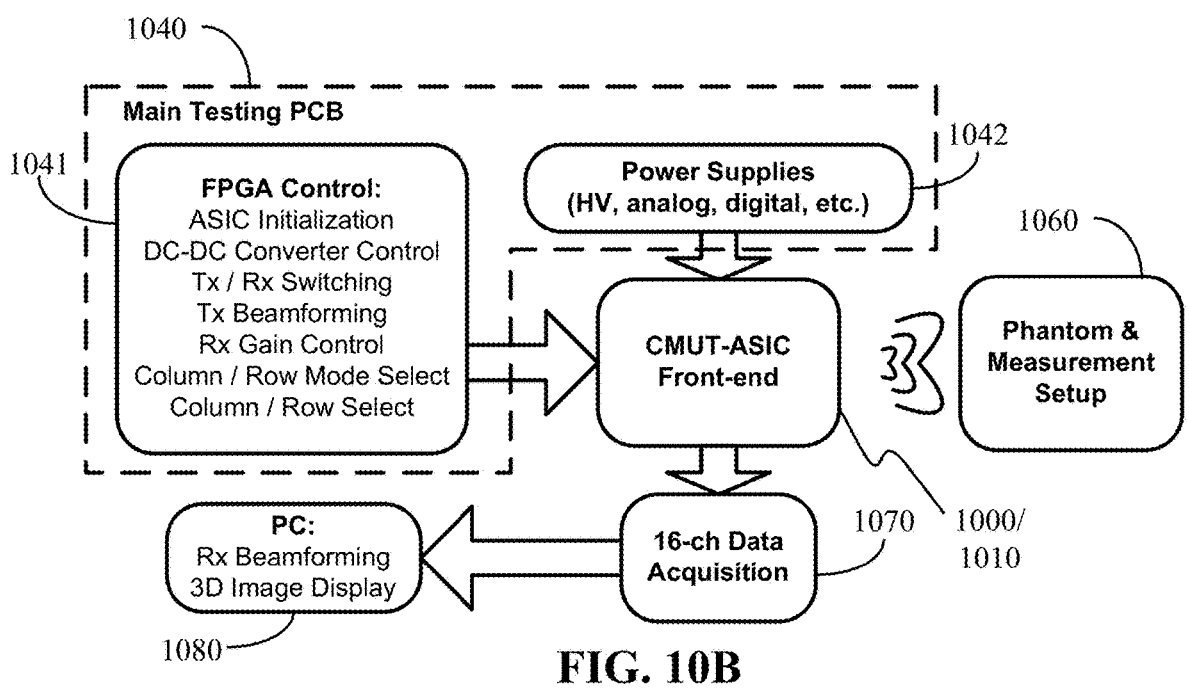
FIG. 10B illustrates a block diagram of the CMUT-ASIC prototype system.

FIG. 10A illustrates a CMUT-ASIC prototype system used in certain experiment examples; and FIG. 10B illustrates a block diagram of the CMUT-ASIC prototype system. Referring to FIG. 10A, a 2D CMUT 1000 is pixel matched and flip chip bonded to an ASIC 1010 through a PCB interposer 1020. Connection I/Os 1030 from the PCB interposer connect control and power signals from a main testing PCB 1040 to the ASIC 1010 (and CMUT 1000). As shown in FIG. 10B, the main testing PCB 1040 for the test set-up includes FPGA control 1041 for ASIC initialization, DC-DC converter control, Tx/Rx switching, Tx Beamforming, Rx Gain control, column/row mode select, and column/row select. It is expected that any or all of these elements can be provided on chip (as part of the ASIC) or as a separate chip bonded or otherwise electrically connected to the ASIC for non-test operation. The main testing PCB 1040 for the test set-up further includes power supplies 1042 for the high voltage (HV) devices as well as the analog and digital components.

As part of the test set up, the CMUT 1000 is disposed in a tank 1050 with vegetable oil 1055 along with phantom and measurement set-up elements 1060 such as a holder 1061 and 3D translation stage 1062. In the test set-up, output from the CMUT-ASIC 1000/1010 is acquired by a data acquisition unit 1070 and provided to a computer 1080 for analysis and display.

Figure 11B:
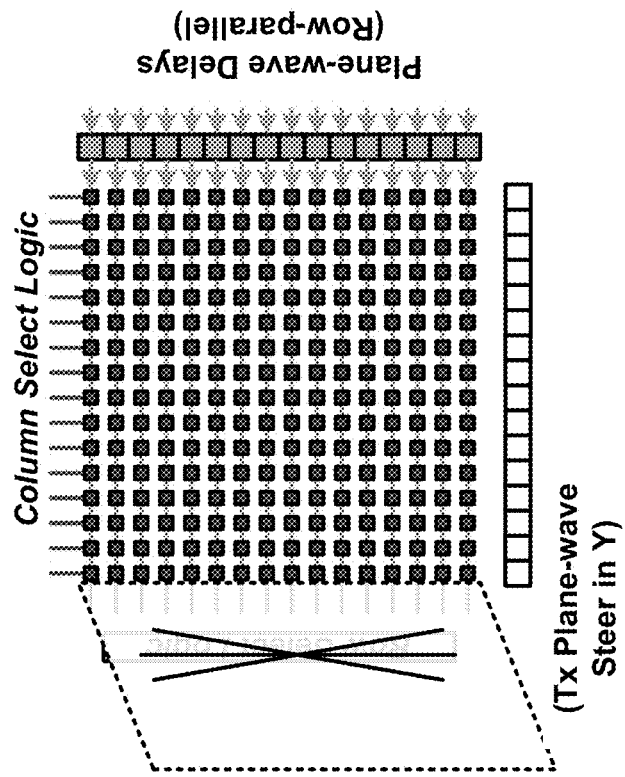
FIG. 11B illustrates the Tx aperture configured in row-parallel mode for plane-wave acoustic excitations with wave-front angles steered along the elevation (Y) direction.
Figure 11A:
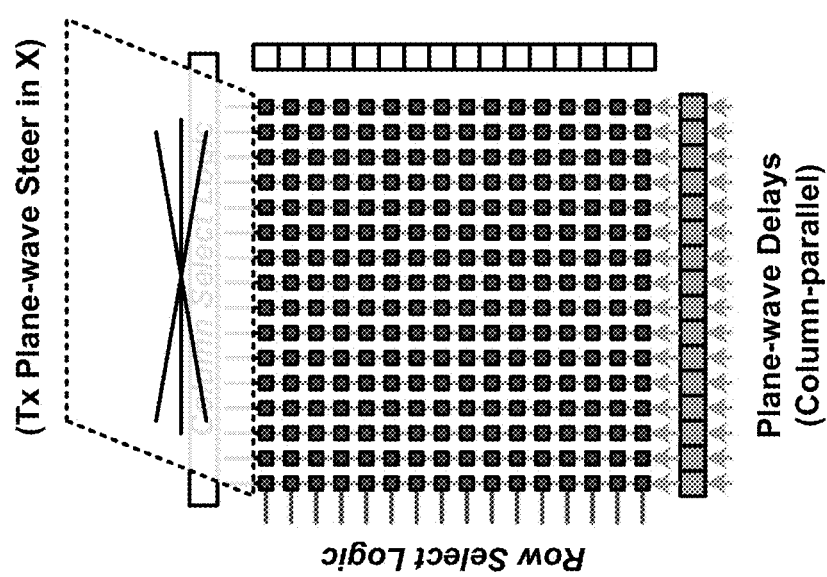
FIG. 11A illustrates the transmit (Tx) aperture configured in column-parallel mode for plane-wave acoustic excitations with wave-front angles steered along the azimuth (X) direction.
Figure 11C:
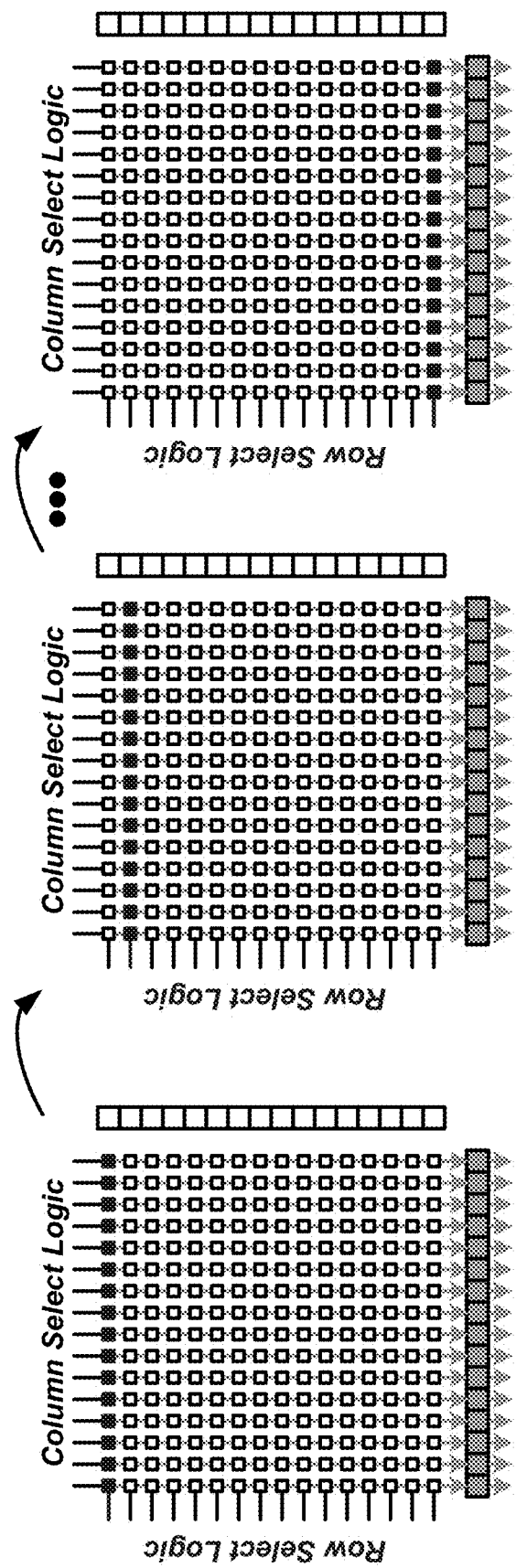
FIG. 11C illustrates the receive (Rx) aperture activated row-by-row in column-parallel mode.

Example—Beamforming for 3D Plane-Wave Coherent Compounding 3D plane-wave coherent compounding (PWCC) can be accomplished using the column-row-parallel architecture. Because of the parallelism along both column and row directions, the column-row-parallel architecture can extend the 2D plane-wave operation into 3D, and perform fast frame rate imaging with 3D plane-wave coherent compounding (PWCC3D). FIGS. 11A-11C illustrate beam-steering for PWCC. In the illustrated example, a 16×16 CMUT-ASIC is programmed such that all array elements are active during transmit to form plane-waves steered at different angles.

FIG. 11A illustrates the Tx aperture configured in column-parallel mode for plane-wave acoustic excitations with wave-front angles steered along the azimuth (X) direction; each column contains 16 active elements in parallel and is driven by a Tx pulser driver at the column side. The 16 column drivers are programmed to supply a linear delay profile with respect to each other, thus generating plane-wave wavefronts tilted at different angles ($\alpha 1 \ldots \alpha p$) along X direction, implementing the azimuth plane-wave steering. Similarly, to achieve steering along the elevation (Y) direction, as shown in FIG. 11B, the Tx aperture is arranged in row-parallel mode, and 16 elements along the same row are driven by the shared Tx pulser driver at the row side. The 16 row drivers control the plane-wave tile angle along Y ($\beta 1 \ldots \beta q$). To collect ultrasound echo signals reflected at a given Tx angle, the Rx aperture is activated row-by-row in column-parallel mode as shown in FIG. 11C (which shows a first row, a second row, and a final row data acquisition). In each reception, 16 analog waveforms are acquired from the activated elements, and the full 256 echo waveforms are acquired after 16 Tx-Rx repetitions.

Figure 12:
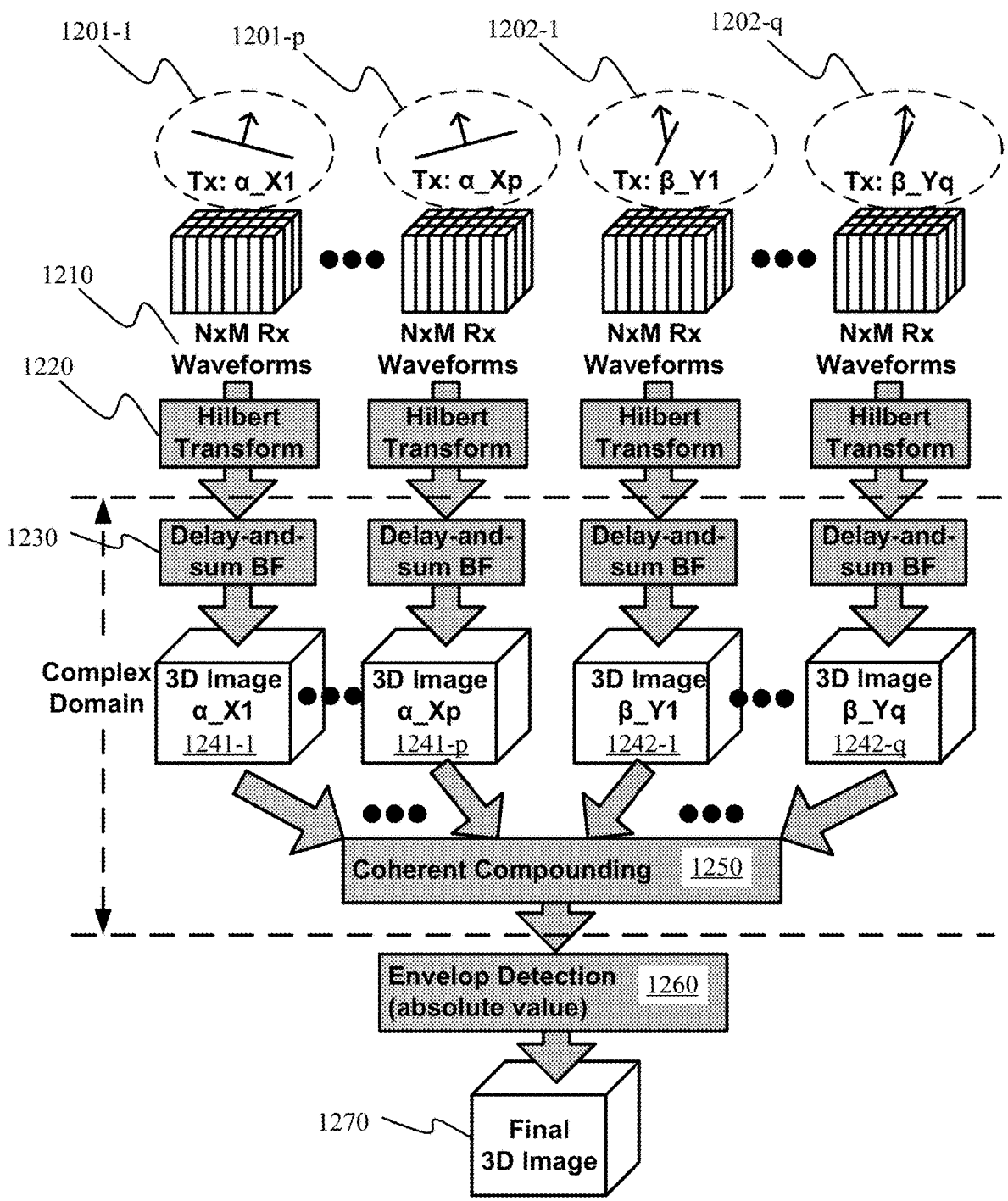
FIG. 12 illustrates a 3D beam-forming signal processing flow for 3D plane-wave coherent compounding (PWCC3D) on the column-row-parallel architecture.

FIG. 12 illustrates a 3D beam-forming signal processing flow for PWCC3D on the column-row-parallel architecture. Referring to FIG. 12, Rx data for all Tx angles along the azimuth (X) direction (1201-1 through 1201-*p*) and the elevation (Y) direction (1202-1 through 1202-*q*) are collected (1210) (e.g., through configurations illustrated in FIGS. 11A-11C). A Hilbert transform $$\left(\text{generally given as } g(y) = \mathcal{H}[f(x)] = \frac{1}{\pi} PV \int_{-\infty}^{\infty} \frac{f(x)dx}{x-y}\right)$$

can be performed with respect to the Rx data from each of the Tx angles to help derive the analytic representation of the received signals (1220). Then, delay-and-sum beamforming values can be generated (1230). For example, given a Tx planewave angle along azimuth a, or elevation 13, the delay-and-sum beamforming delay values, which represent the time-of-flight (where c is sound speed) from center of the transducer array (0; 0; 0) to an image voxel at (x; y; z) is given as follows:

$$\begin{cases} T_{TX\_azimuth}(\alpha, x, y, z) = (z \cdot \cos\alpha + x \cdot \sin\alpha)/c, \\ T_{TX\_elevation}(\beta, x, y, z) = (z \cdot \cos\beta + y \cdot \sin\beta)/c. \end{cases}$$

The time-of-flight back to the receiving element at (x1; y1; 0) can then be given as follows:

$$\tau_{RX}(x_1, y_1, x, y, z) = \sqrt{z_2 + (x-x_1)^2 + (y-y_1)^2}/c$$

Using the delay-and-sum beamforming values, 3D images in complex value are formed for every Tx angle (1241-1 through 1241-p and 1242-1 through 1241-q). Coherent compounding is then carried out across all angles, by adding voxel values in complex domain (1250). The final compounded 3D image 1270 is obtained by taking the magnitude of the complex value voxels (envelope detection) (1260). Steps 1220, 1230, 1250, and 1260 may be carried out as a software process. The software process may be carried out at a computing device that processes the data received via the ASIC (e.g., at PC 1080 of FIG. 10B after being collected by a data acquisition unit 1070).

Through such a processing scheme, a software beamformer can be implemented that is low-power and flexible with speed and quality tradeoff. Data acquisition is only performed once, while beam-formation on each voxel is independent and utilizes the same set of data. One can perform coarse imaging over a large space; and a higher definition second-pass over a smaller space, after spotting features of interest.

Figure 13A:
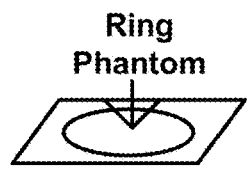
FIG. 13A shows a representation indicating that the volumetric images of the metal ring phantom are shown as a cross-sectional image of a horizontal slice.
Figure 13B:
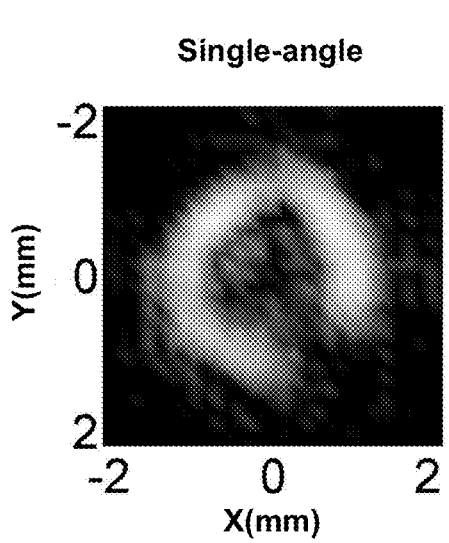
FIG. 13B shows the horizontal slice image from a single-angle Tx plane wave.
Figure 13C:
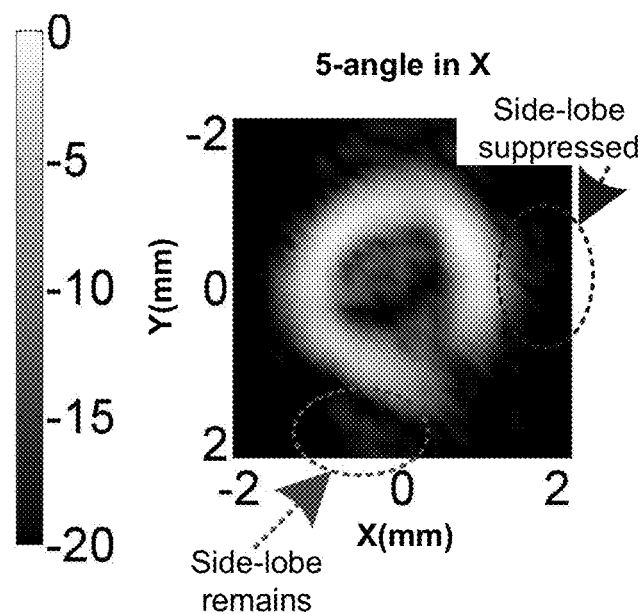
FIG. 13C shows the horizontal slice from 5-angle in the azimuth direction.
Figure 13D:
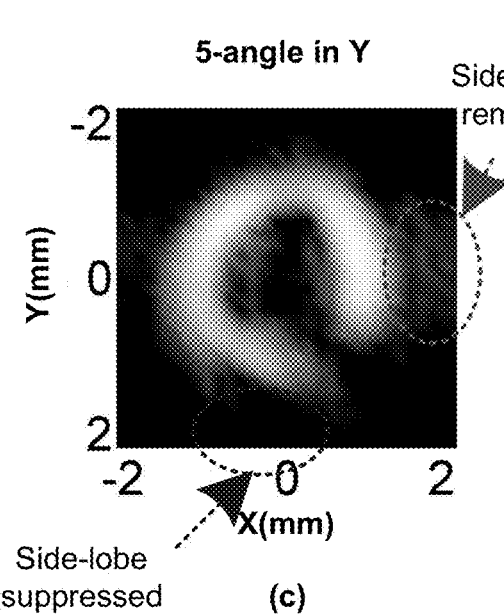
FIG. 13D shows the horizontal slice from 5-angle in the elevation direction.
Figure 13E:
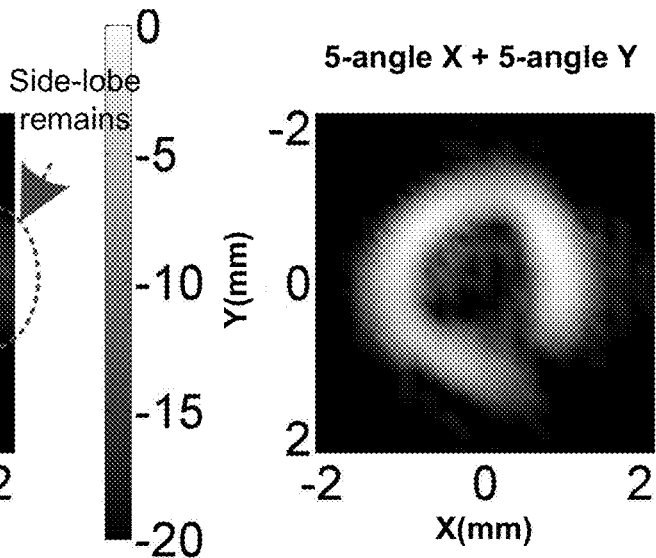
FIG. 13E shows a horizontal slice from compounded plane-waves (compound of azimuth and elevation).

To illustrate the PWCC3D implementation, measured wire and ring images were obtained using the test set-up described with respect to FIGS. 10A and 10B. The volumetric images of a metal ring phantom were acquired by the 16×16 CRP CMUT-ASIC front-end assembly. The ring was placed horizontally above the transducer surface at a distance of 7.5 mm. The Tx pulsation was 2 bursts of 8.33 MHz pulses; a constant F-number of 1.75, and rectangular windows were used for Tx and Rx apodization. FIG. 13A shows a representation indicating that the volumetric images of the metal ring phantom are shown as a cross-sectional image of a horizontal slice. FIG. 13B shows the horizontal slice image from a single-angle Tx plane wave. FIG. 13C shows the horizontal slice from 5-angle in the azimuth direction. As indicated in the figure, the side-lobe remains in one direction (X direction), while the side-lobe is suppressed in the other direction (Y direction). FIG. 13D shows the horizontal slice from 5-angle in the elevation direction. As indicated in the figure, the side-lobe remains in one direction (Y direction), while the side lobe is suppressed in the other direction (X direction). FIG. 13E shows a horizontal slice from compounded plane-waves (compound of azimuth and elevation).

The single-angle image of FIG. 13B can be compared against the images compounded with 5 X-angles and 5 Y-angles at (−6.7°, −3.3°; 0°; 3.3°; 6.7°) shown in FIGS. 13C and 13D. The 10-angle compounded cross-sectional image of FIG. 13E shows higher contrast and lower side-lobes.

FIG. 14A shows a representation indicating that the volumetric images of the metal ring phantom are shown as a cross-sectional image of a vertical slice. FIG. 14B shows the vertical slice image from a single-angle Tx plane wave. FIG. 14C shows the vertical slice from compounded plane-waves (compound of azimuth and elevation). FIG. 14D shows a lateral resolution plot of the single-angle ring image. FIG. 14E shows a lateral resolution plot from the compounded image showing suppressed side-lobes. As shown in FIGS. 14D and 14E, it can be seen that the side-lobes in the center of the ring is improved by 6 dB with 10-angle coherent compounding (from −7.3 dB to −13.3 dB).

Figure 15A:
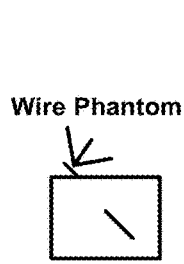
FIG. 15A shows a representation indicating that the volumetric images of the wire phantom are shown as a cross-sectional image of the wire.
Figure 15B:
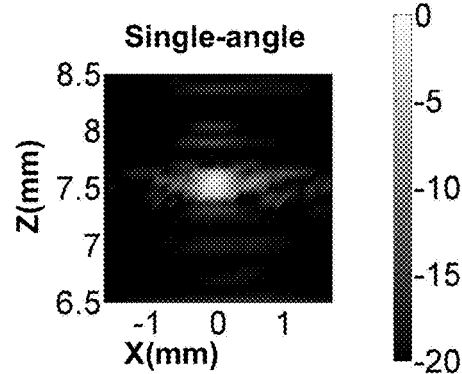
FIG. 15B shows the cross-sectional slice image from a single-angle Tx plane wave.
Figure 15C:
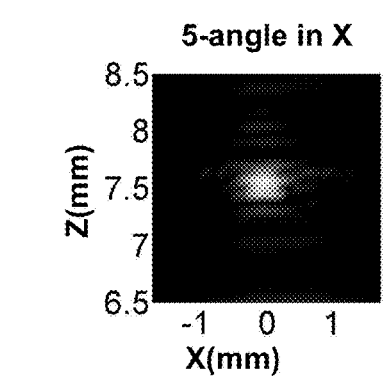
FIG. 15C shows the cross-sectional slice from a 5-angle in the azimuth direction.
Figure 15D:
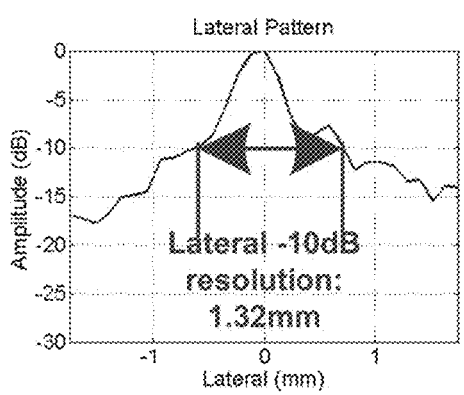
FIG. 15D shows a lateral resolution plot of the single-angle wire phantom image.
Figure 15E:
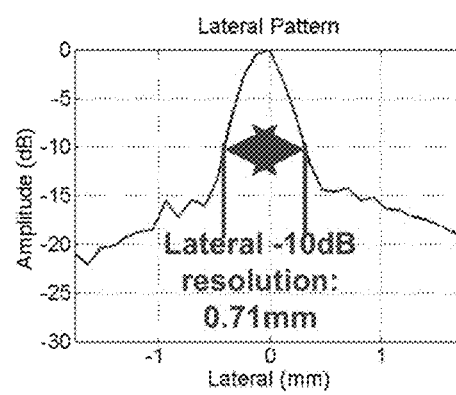
FIG. 15E shows a lateral resolution plot from the compounded image showing suppressed side-lobes.

Experimental images were also taken of a wire phantom. FIG. 15A shows a representation indicating that the volumetric images of the wire phantom are shown as a cross-sectional image of the wire. FIG. 15B shows the cross-sectional slice image from a single-angle Tx plane wave. FIG. 15C shows the cross-sectional slice from a 5-angle in the azimuth direction. FIG. 15D shows a lateral resolution plot of the single-angle wire phantom image. FIG. 15E shows a lateral resolution plot from the compounded image showing suppressed side-lobes. As shown in FIGS. 15D and 15E, there is a 46% improvement of −10 dB lateral resolution (from 1.32 mm to 0.71 mm) with 10-angle compounding. A 10 kHz pulse repetition frequency (PRF) was used for the 10-angle compounding scheme in the experiments, leading to a frame rate of 62.5 volume/s. The frame rate decreases linearly with increase in the array size, or number of plane-wave angles, to trade for better image quality.

Figure 15F:
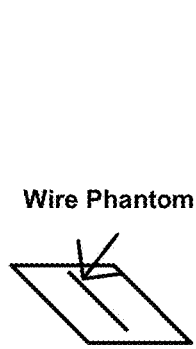
FIG. 15F shows a representation indicating that the volumetric images of wire phantom are shown as a longitudinal cross-section image.
Figure 15G:
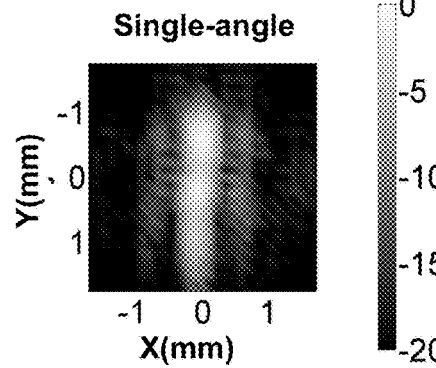
FIG. 15G shows the longitudinal cross-section image from a single-angle Tx plane wave.
Figure 15H:
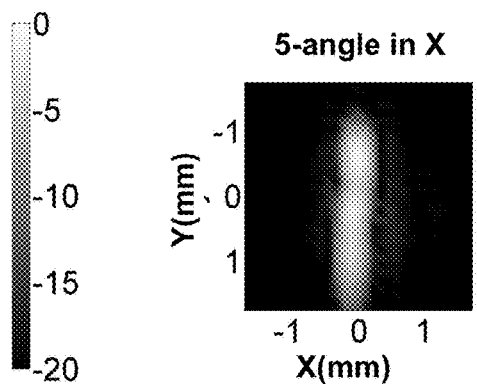
FIG. 15H shows the longitudinal cross-section image from a 5-angle in the azimuth direction.

FIG. 15F shows a representation indicating that the volumetric images of wire phantom are shown as a longitudinal cross-section image. FIG. 15G shows the longitudinal cross-section image from a single-angle Tx plane wave. FIG. 15H shows the longitudinal cross-section image from a 5-angle in the azimuth direction.

Example—Second Order Harmonic Distortion Cancelation for Tissue Harmonic Imaging In addition to being able to perform PWCC, tissue harmonic imaging can be accomplished using CMUT despite its nonlinear electrostatic actuation mechanism, where excessive second order harmonic distortion (HD2) is generated during transmit. Second harmonic inversion can be performed using two consecutive I and Q pulses for HD2 cancelation. The described column-row-parallel architecture can be used to generate an interleaved checker board aperture for second harmonic inversion in one transmission stage. The I&Q excitations can reduce Tx second harmonic distortion from both transducers and circuits with any arbitrary pulse shapes, suppressing CMUT non-linearity for ultrasonic harmonic imaging.

Figure 16:
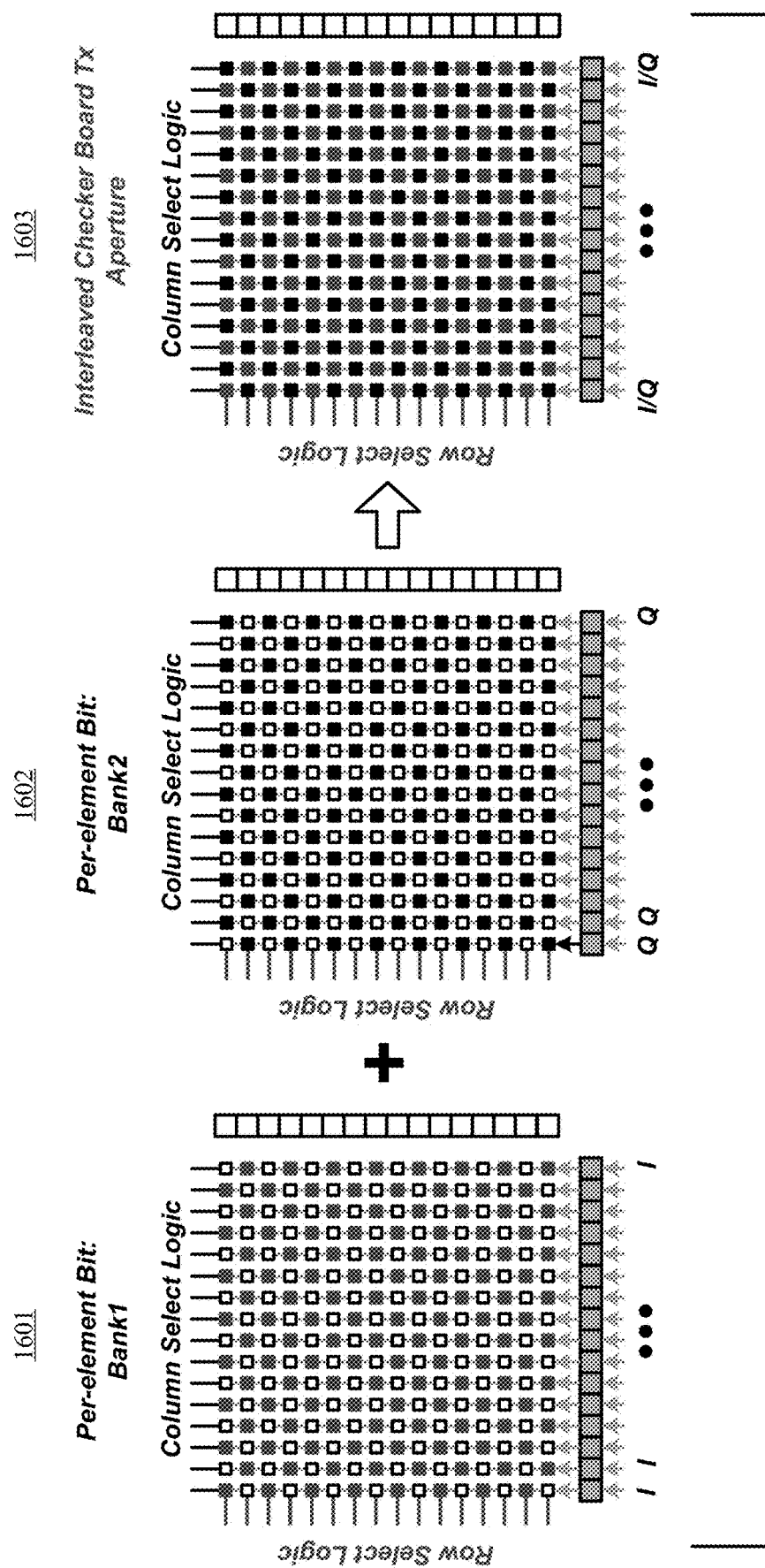
FIG. 16 illustrates an interleaved checkerboard aperture scheme with I&Q Tx excitations.

FIG. 16 illustrates a checkerboard aperture scheme with I&Q Tx excitations. Referring to FIG. 16, a first pulse (I pulse) can be carried out using a pattern 1601 stored in a first bank of Tx per-element enable bits and a second pulse (Q pulse) can be carried out using a pattern 1602 stored in a second bank of Tx per-element enable bits. These two patterns 1601, 1602 are preprogrammed into the two banks so that an interleaved checker board pattern 1603 is generated. By quickly switching active Tx apertures between the two banks, the column pulser drivers are able to drive Bank1 elements with I(t) pulses and Bank2 with Q(t) simultaneously as shown in FIG. 16, where Q(t) is time-delayed by a quarter pulse cycle with respect to I(t). The pulse signals go through a nonlinear quadratic transfer function into the emitted acoustic pressure.

For any arbitrary pulse shape, the fundamental component of acoustic pressure generated by I(t) and Q(t) are out of phase by $\pi/2$, leading to a 3 dB intensity reduction compared to a full array excitation; meanwhile, the 2nd harmonic component are out of phase by $\pi$ and cancel each other. It should be noted that not only the 2nd second harmonic, but the 6th, 10th, 14th, . . . (i.e., (2+4*k)-th, where k=0; 1; 2; . . . ) are also out of phase by integer multiples of $\pi$. Reductions in 6th and 10th components were observed in measurement, while higher harmonics are too weak to see. Furthermore, because a general 2nd-order distortion model is assumed, this method applies not only to CMUT, but also other sources of nonlinearity—for example, HD2 introduced from pulse rise/fall time asymmetry due to circuit mismatches. To minimize the grating lobes and perform optimized HD2 cancelation, the element pitch of the interleaved checker board patterns are made smaller or approximately equal to the ultrasound wavelength.

Figure 17B:
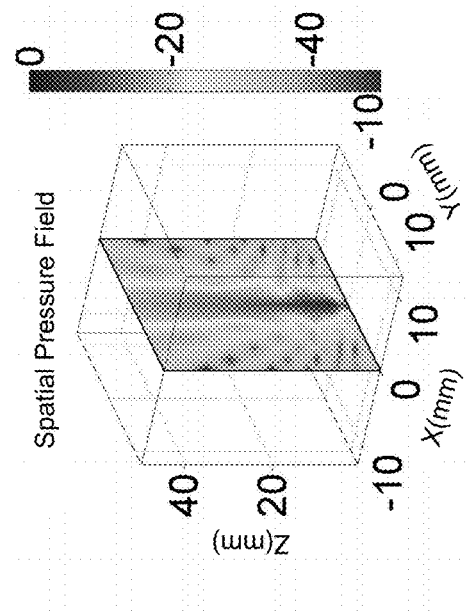
FIGS. 17A-17D provide a simulation comparison spatial acoustic pressure intensity between a conventional method and an I&Q method using the described column-row-parallel architecture in the interleaved checker board aperture.
Figure 17D:
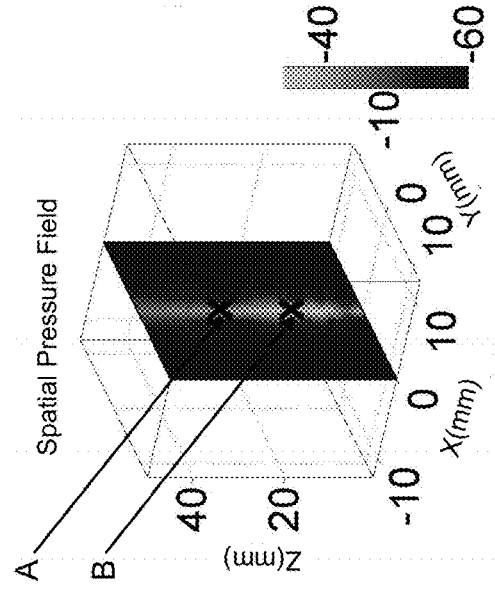
Figure 17A:
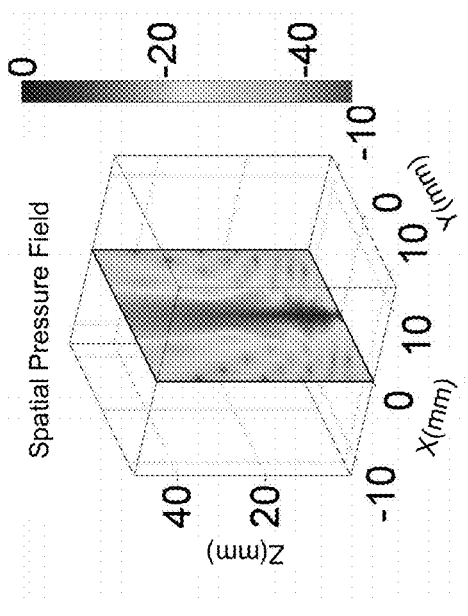

Simulation and measurements were carried out to show the effectiveness of the checkerboard pattern verify the theory. Various configurations are used to show that I&Q method is a general and broadband technique: pulse shapes (2-/3-level), number of bursts (2-20), frequencies (2.1/2.8/4.2 MHz), pulse amplitudes (10/20/30 Vpp), and CMUT bias voltages (20/30/40V) were varied. FIGS. 17A-17D provide a simulation comparison spatial acoustic pressure intensity between a conventional method and an I&Q method using the described column-row-parallel architecture in the interleaved checker board aperture. FIG. 17A shows the spatial acoustic pressure intensity for a fundamental component (A) of the emitted pressure field using a conventional method. FIG. 17B shows the spatial acoustic pressure intensity for the fundamental component using the I&Q method. As can be seen in FIGS. 17A and 17B, the conventional method produces a field with 3 dB higher intensity than I&Q.

Figure 17C:
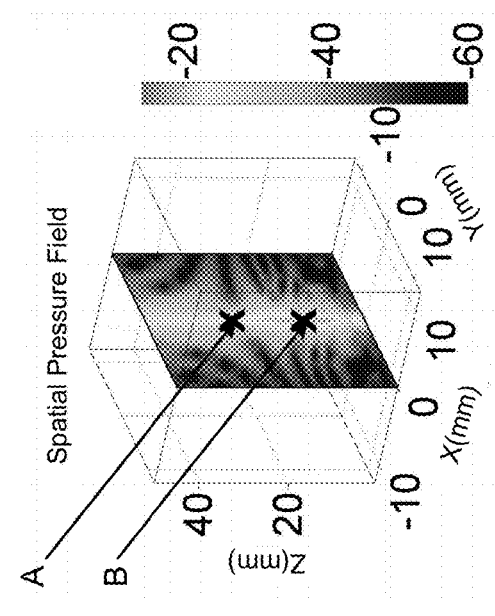

FIG. 17C shows the spatial acoustic pressure intensity for the second order harmonic distortion (HD2) component using the conventional method. FIG. 17D shows the spatial acoustic pressure intensity for the HD2 component using the I&Q method. As can be seen in FIGS. 17C and 17D a large HD2 suppression is available from I&Q. The measured normalized field intensity at the same spatial locations as in simulation are summarized in the following Table, confirming that the I&Q method has 3 dB less fundamental intensity but over 20 dB HD2 performance improvement.

|  | HD2 Reduction | Fundamental Loss |
|---|---|---|
| Simulation |  |  |
| "A" (0, 0, 30.3)mm | −19.7 dB | −3.0 db (the whole space) |
| "B" (0, 0, 10.2)mm | −19.7 dB |  |
| Measurement |  |  |
| "A" (0, 0, 30.3)mm | −21.7 dB | −3.4 dB |
| "B" (0, 0, 10.2)mm | −22.1 dB | −3.2 dB |

For the measurements, a 10×10 CMUT sub-array was used instead of the 16×16 array (due to non-functional CMUT elements in the prototype).

Example—Annular Ring Apertures for Forward-Looking Imaging Applications

In addition to the flexibility of performing plane-wave coherent compounding and performing an I&Q method, the column-row-parallel architecture can generate annular ring apertures. Forward looking (as opposed to side-looking) ultrasonic imaging systems can be used for intravascular (within the blood vessel) and intracardiac (within the heart) visualizations. A miniaturized imaging system can be mounted onto the tip of a catheter, which provides minimally invasive diagnosis, interventions or treatments in medical procedures.

Annular ring apertures are suitable to realize forward-looking imaging. Although dedicated annular ring arrays are available by custom fabrication, a general purpose 2D array with the described Column-Row-Parallel architecture can achieve similar results. The full 2D array—as opposed to a dedicated annular ring array—provides even more flexibility, since more rings can be formed within the regular 2D aperture.

Figure 18E:
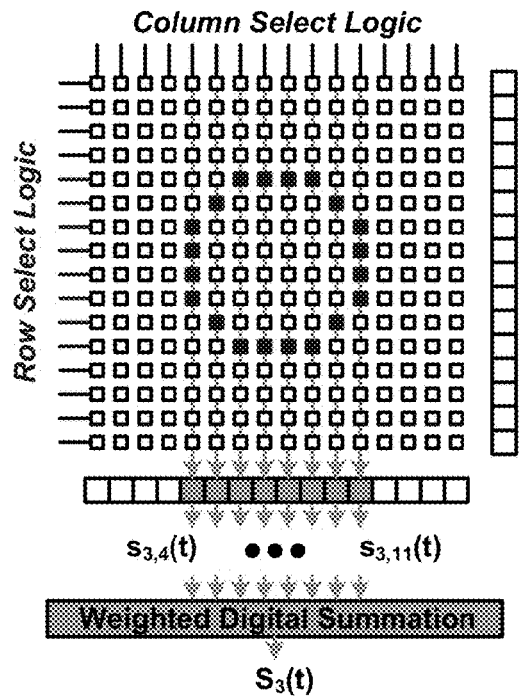

The 2D array with the Column-Row-Parallel architecture can form a circular aperture or an annular ring aperture by programming the per-element bits under each element. FIGS. 18A-18F illustrate an example annular ring configuration and FIGS. 19A-19F illustrate an example off-center annular ring configuration. For annular ring imaging, a circular Tx aperture is used for transmit and four concentric annular rings with different diameters can be activated as Rx apertures, as shown in FIG. 18A (and similarly in FIG. 19A). The Tx elements are supplied with the same delay value "D" as shown in FIG. 18B (and similarly in FIG. 19B), so that the whole circular aperture is driven in-phase and emits a broad ultrasound beam. The Rx elements' analog outputs are also combined in parallel along the column, and by digitally summing the weighted waveforms from all column buffers, one echo waveform may be collected for each annular ring, as shown by the four configurations in FIGS. 18C-18F (and similarly in FIGS. 19C-19F). The weight for each column is the number of active elements along the column. The weighted digital summation block can be described by the following function:

$$S_m(t) = \sum_{k=0}^{15} n_k \cdot s_{m,k}(t), m = 1, 2, 3, 4.$$

Figure 18F:
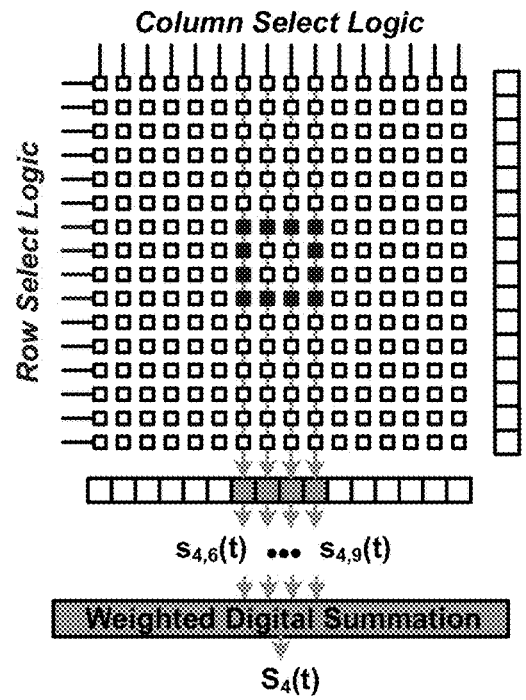
Figure 19A:
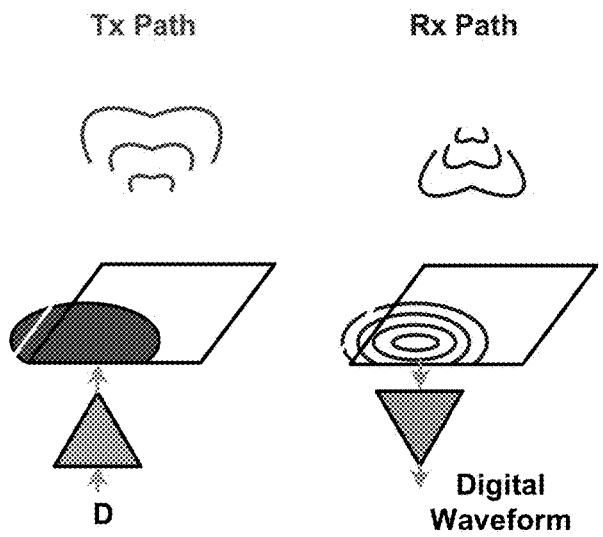
FIGS. 19A-19F illustrate an example off-center annular ring configuration.
Figure 19B:
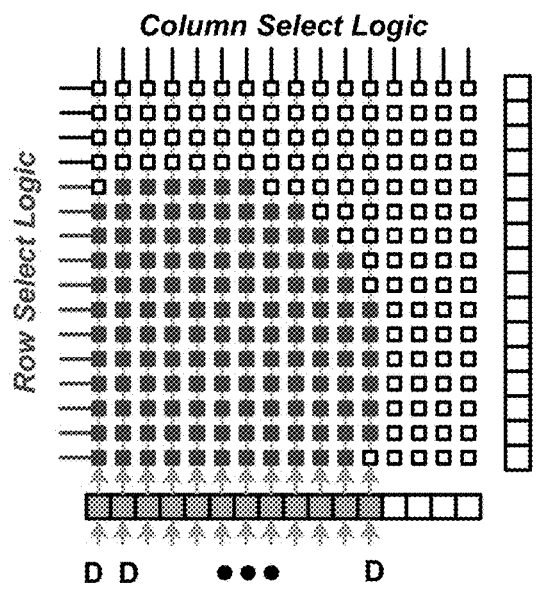
Figure 19C:
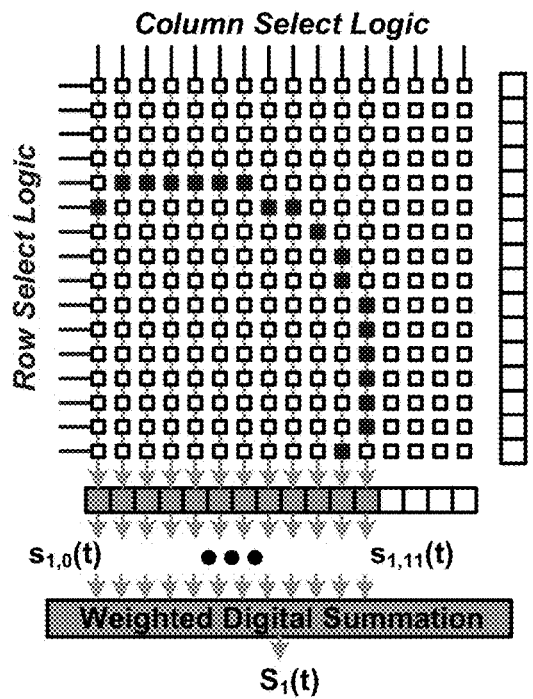
Figure 19D:
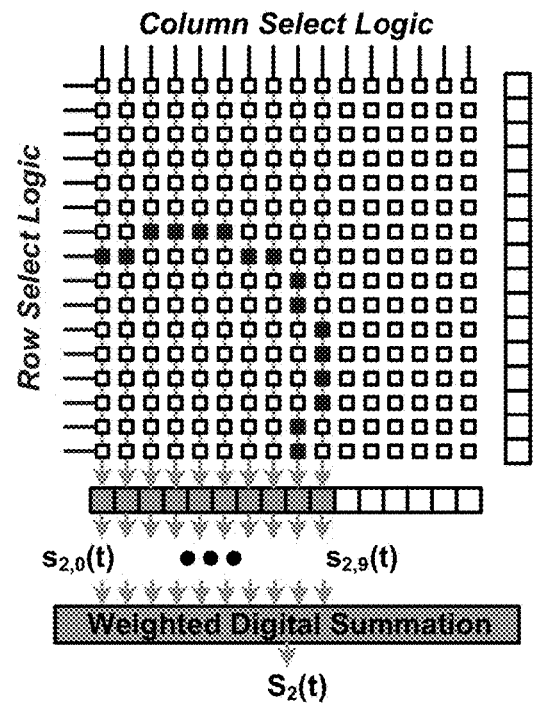
Figure 19E:
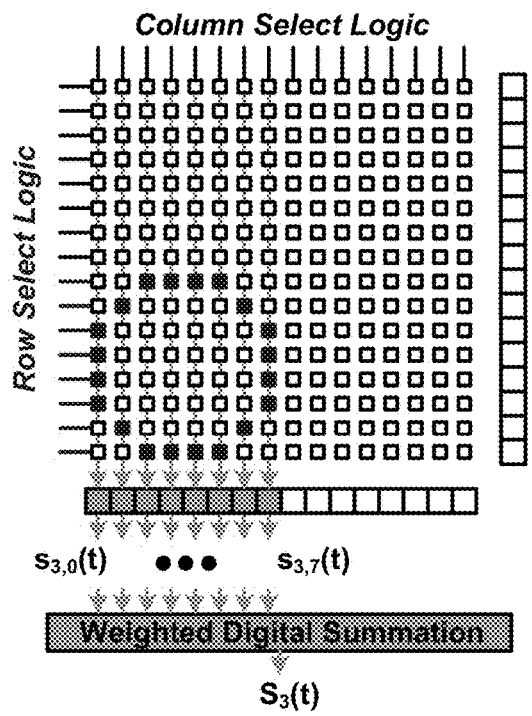
Figure 19F:
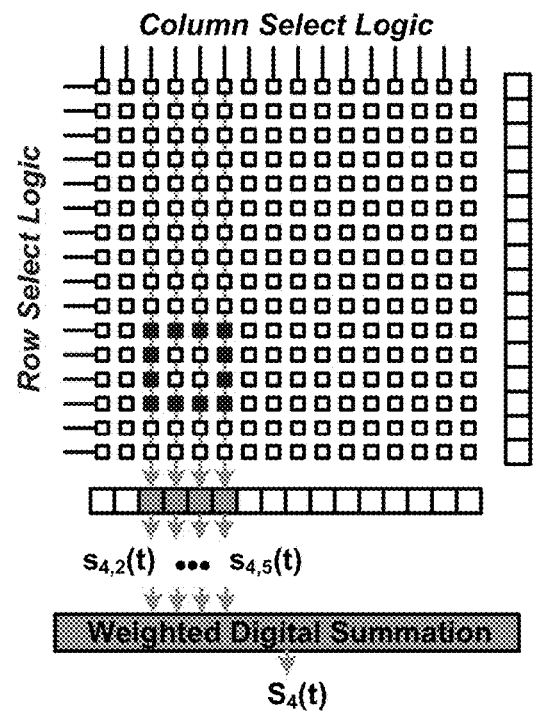

For the smallest ring, shown in FIG. 18F, the number of active elements for columns $s_6(t) \sim s_9(t)$ are 4, 2, 2, and 4, respectively. Therefore the weighted summation should be:

$$S_4(t) = 4 \times s_{4,6}(t) + 2 \times s_{4,7}(t) + 2 \times s_{4,8}(t) + 4 \times s_{4,9}(t).$$

Figure 20:
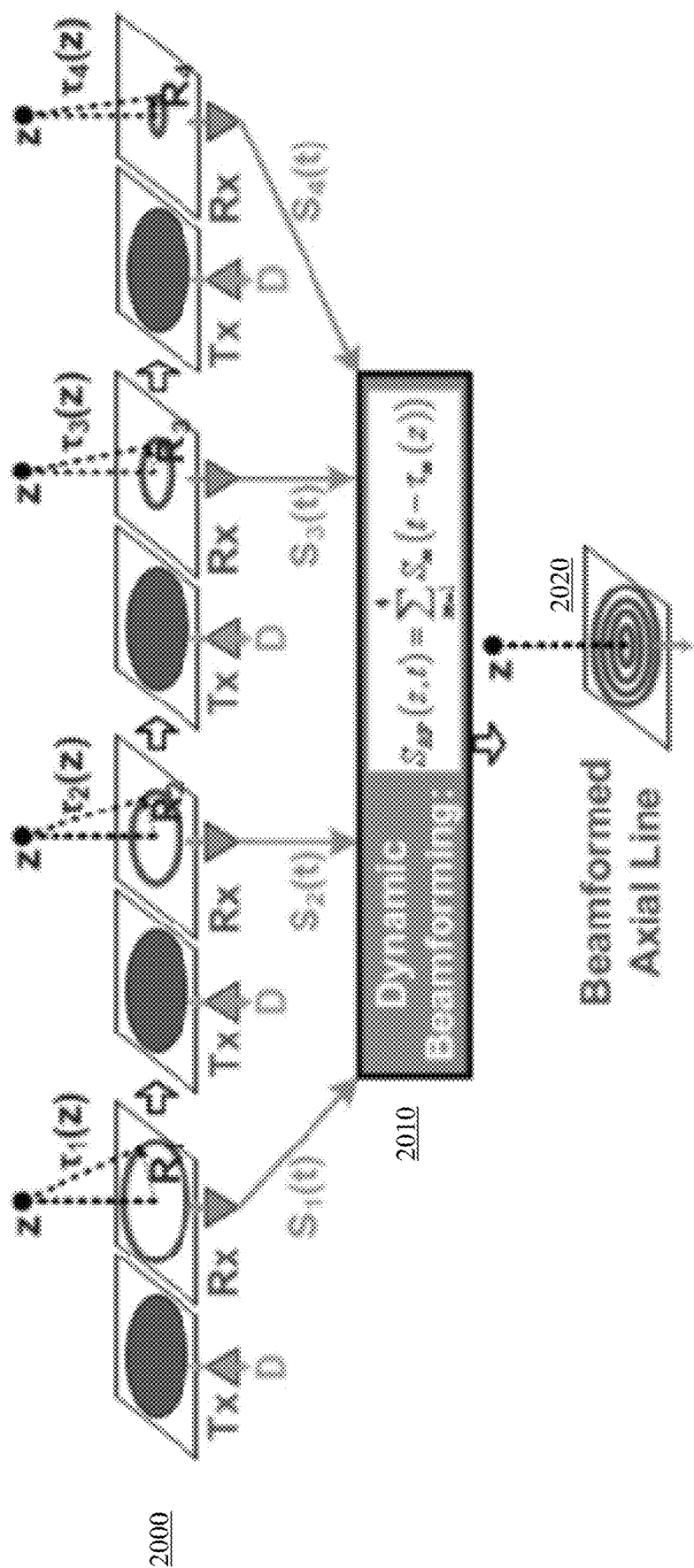
FIG. 20 shows an annular ring mode dynamic beam formation scheme.

The four Rx annular rings are activated over four consecutive Tx transmits ($S_1(t)$, $S_2(t)$, $S_3(t)$, and $S_4(t)$) (2000) as shown in FIG. 20. The digital waveforms from the four Rx rings can then be dynamically beamformed (2010) to generate a synthetic A-scan line (2020) along the axial axis of the rings. Because all elements on the same ring have the same time-of-flight to a point on the axial axis, each ring has a natural focus effect along the axial axis. The delay value for a spatial point located at depth z away from the transducer surface, for the ring with a radius of Rm, is calculated as:

$$T_m(z) = \sqrt{z^2 + R_m^2}/c, \; m=1,2,3,4.$$

The beamformed image line along the axial axis thus becomes:

$$S_{BF}(z, t) = \sum_{m=1}^{4} S_m(t - \tau_m(z)).$$

The circular and ring apertures are translated horizontally, so that different axial A-scan lines can be collected to form volumetric images. Examples of translated Tx and Rx apertures are shown in FIGS. 19A-19F, where the annular ring configuration is generated off-center. Here, some edge effect will affect the scan line intensity slightly, but not significantly.

The forward-looking programmable annular ring array can form volumetric images by moving the circular Tx and annular Rx apertures in the 2D array, so that multiple axial lines can be acquired. Both simulation and measurement of a wire phantom were performed, similar to the PWCC3D experiments (such as described with respect to FIGS. 13-15). For the experiments, The wire phantom is 0.48 mm in diameter and was placed at 10.5 mm away from the transducer surface, horizontal to the surface. Transmit pulsation is 2 bursts of 8.33 MHz pulses. The volumetric images are displayed at 20 dB dynamic range. A total of 81 circular Tx apertures are swept through the 2D array, acquiring data for 81 axial lines. With four beamforming annular rings at each Tx aperture location, a total of 324 transmit-receive repetitions are used to acquire a full set of volumetric data. The acquisition time and volume rate for the annular ring imaging system can be calculated as follows.

$$\text{Acquisition Time} = \frac{(\# \text{ Axial Lines}) \times (\# \text{ Annular Rings})}{PRF},$$

$$\text{Volume Rate} = \frac{PRF}{(\# \text{ Axial Lines}) \times (\# \text{ Annular Rings})}.$$

The acquisition time again scales linearly with respect to the number of axial lines in the volumetric image, or number of annular rings used for beam-formation.

Figure 23C:
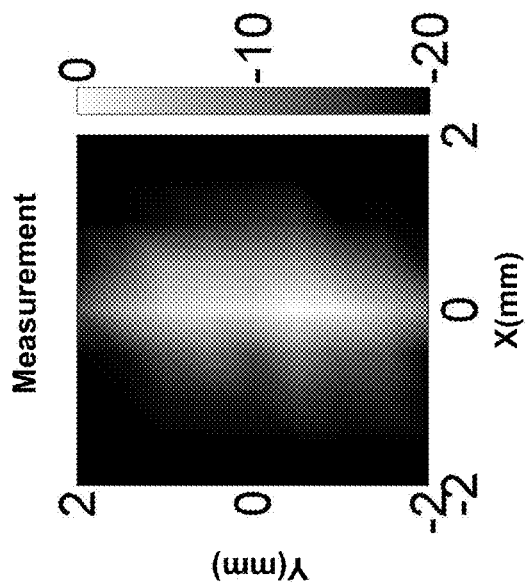
FIG. 23C shows the cross-sectional slice image from the measured XY slice.
Figure 23B:
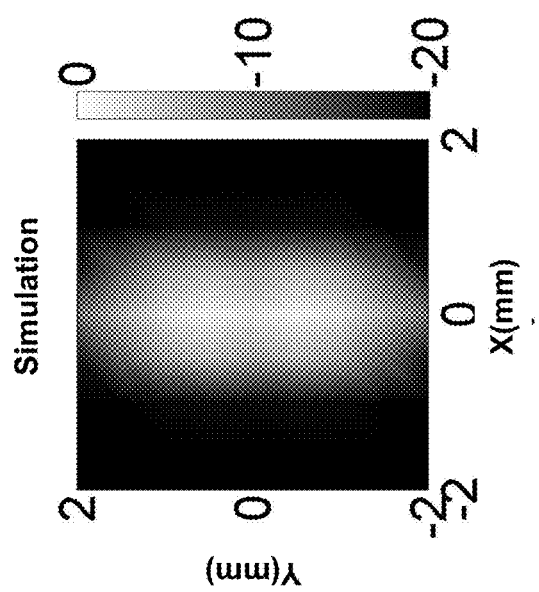
FIG. 23B shows the cross-sectional slice image from a simulated XY slice.
Figure 23A:
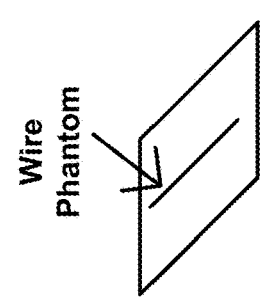
FIG. 23A shows a representation indicating that the volumetric images of the wire phantom are shown as a horizontal cross-section of a longitudinal image of the wire (XY plane).

The volumetric images from simulation and measurement are shown in FIGS. 21A-21C, 22A-22C, and 23A-23C. FIG. 21A shows a representation indicating that the volumetric images of the wire phantom are shown as a cross-sectional image of the wire (XZ plane). FIG. 21B shows the cross-sectional slice image from a simulated XZ slice; and FIG. 21C shows the cross-sectional slice image from the measured XZ slice. FIG. 22A shows a representation indicating that the volumetric images of the wire phantom are shown as a vertical cross-section of a longitudinal image of the wire (YZ plane). FIG. 22B shows the cross-sectional slice image from a simulated YZ slice; and FIG. 22C shows the cross-sectional slice image from the measured YZ slice. FIG. 23A shows a representation indicating that the volumetric images of the wire phantom are shown as a horizontal cross-section of a longitudinal image of the wire (XY plane). FIG. 23B shows the cross-sectional slice image from a simulated XY slice; and FIG. 23C shows the cross-sectional slice image from the measured XY slice.

The measured −10 dB lateral resolution (from XZ slice, FIG. 21C) is 1.19 mm and the −10 dB axial resolution (from YZ slice, FIG. 22C) is 0.32 mm. Both numbers are close to the performance measured from PWCC3D images with single-angle plane-wave insonification. Using a 10 kHz PRF, the volume rate is 30.9 volume/s.

It should be understood that the use of a 16×16 array is merely illustrative of one configuration of the described architecture and that larger or smaller arrays may be used to varying effects (and the array is not required to be N×N). Larger arrays may present higher image quality. In addition, the number of annular rings can also be increased; however, volume rate may decrease.

It should be understood that the examples and embodiments described herein are for illustrative purposes only and that various modifications or changes in light thereof will be suggested to persons skilled in the art and are to be included within the spirit and purview of this application.

We claim:

1. An ultrasonic imaging system, comprising:
   an array of transducer elements comprising N rows and M columns; and
   a plurality of transceiver circuits, each transceiver circuit being connected to a corresponding one transducer element of the array of transducer elements and each transceiver circuit comprising:
      a per-element selection logic receiving a row selection signal, a column selection signal, and an enable signal to control operation of the transceiver circuit;
      a first switch controlled by a transmit column select signal from the per-element selection logic;
      a second switch controlled by a transmit row select signal from the per-element selection logic;
      a third switch controlled by a receive column select signal from the per-element selection logic;
      a fourth switch controlled by a receive row select signal from the per-element selection logic;
      a transmitter pulser circuit connected at its output to the transceiver circuit's corresponding one transducer element and connected at its input to the first switch and to the second switch; and
      a receiver low noise amplifier (LNA) selectively connected at its input to the transceiver circuit's corresponding one transducer element and connected at its output to the third switch and to the fourth switch.

2. The system of claim 1, wherein the array of transducer elements is provided on a transducer chip stacked on an application specific integrated circuit (ASIC) chip.

3. The system of claim 1, further comprising:
   a column gate driver connected to the transmitter pulser circuit of each transceiver circuit of a column of transceiver circuits, a total of N column gate drivers being provided;
   a row gate driver connected to the transmitter pulser circuit of each transceiver circuit of a row of transceiver circuits intersecting with the column of transceiver circuits, a total of M row gate drivers being provided;
   a column variable gain amplifier (VGA) buffer connected to the receiver LNA of each transceiver circuit of the column of transceiver circuits, a total of N column VGA buffers being provided; and
   a row VGA buffer connected to the receiver LNA of each transceiver circuit of the row of transceiver circuits, a total of M row VGA buffers being provided.

4. The system of claim 3, wherein the number of rows equals the number of columns, the system further comprising:
   selection logic that connects the 2N total number of the column gate drivers and the row gate drivers to a total of N input/output ports.

5. The system of claim 3, wherein each of the N column VGA buffers and each of the M row VGA buffers comprises:
   a differential amplifier; and
   a cancelation loop buffer connected to receive at least an output of the differential amplifier and output a cancelation loop signal at the output of the differential amplifier.

6. The system of claim 3, wherein each of the N column VGA buffers and each of the M row VGA buffers comprises:

a differential amplifier; and
a cancelation loop buffer connected to receive at least an output of the differential amplifier and output a cancelation loop signal to a VGA input of the differential amplifier at an output of a corresponding LNA.

7. The system of claim 3, further comprising:
at least one analog-to-digital converter (ADC);
at least one digital-to-analog converter (DAC); and
a cancelation loop for each of the N column VGA buffers, and each of the M row VGA buffers, the cancelation loop connecting a VGA output to the ADC and feeding back a digitized output from the ADC through the DAC to a VGA input at an output of a corresponding receiver LNA.

8. The system of claim 1, further comprising:
a row-select and column-select control logic connected to the plurality of transceiver circuits for selecting at least one row and at least one column; and
at least one register bank connected to the row-select and column-select control logic.

9. The system of claim 8, further comprising:
an enable select logic chain connected to the per-element selection logic for the plurality of transceiver circuits to provide the enable signal for each transceiver circuit; and
at least one extended register bank connected to one end of the enable select logic chain to shift the enable program through the enable signal logic chain.

10. The system of claim 9, wherein the per-element selection logic provides selective element activation at a per-element level to form arbitrary transmit or receive apertures according to the enable signal.

11. The system of claim 1, further comprising:
a total of N column gate drivers, each column gate driver connected to a corresponding column of transceiver circuits;
a total of M row gate drivers, each row gate driver connected to a corresponding row of transceiver circuits,
a total of N column variable gain amplifier (VGA) buffers, each column VGA buffer connected to a corresponding column of transceiver circuits; and
a total of M row VGA buffers, each row VGA buffer connected to a corresponding row of transceiver circuits.

12. The system of claim 11, wherein for each transceiver circuit:
the transmitter pulser circuit is selectively connected to a column-shared column gate driver of the N column gate drivers and is selectively connected to a row-shared row gate driver of the M row gate drivers; and
the LNA is selectively connected to a column-shared column VGA buffer of the M column VGA buffers and is selectively connected to a row-shared row VGA buffer of the N row VGA buffers.

13. The system of claim 12, wherein the array of transducer elements activate with interleaved checkerboard patterns with I and Q excitations from appropriate column gate drivers of the N column gate drivers or appropriate row gate drivers of the M row gate drivers.

14. The system of claim 12, wherein the array of transducer elements activate to form at least one annular ring aperture.

15. The system of claim 12, wherein the system is activated in column-parallel mode by applying relative delays to selected ones of the column gate drivers to perform azimuth beam-formation, and outputting signals received by selected ones of the column VGA buffers.

16. The system of claim 12, wherein the system is activated in row-parallel mode by applying relative delays to selected ones of the row gate drivers to perform elevation beam-formation, and outputting signals received by selected ones of the row VGA buffers.

17. The system of claim 12, wherein defective channels are removed by sequentially turning on and off, from each channel of the plurality of transceiver circuits, a transistor of the pulser circuit that selectively connects a ground signal to the transceiver circuit's corresponding transducer element; storing a per-element enable bit associated with any defective channels determined through leakage current from the sequentially turning on and off of the transistor; and
using the per-element enable bit as the enable signal during operation of the system.

* * * * *